United States Patent [19]
Crosby et al.

[11] Patent Number: 5,292,340
[45] Date of Patent: Mar. 8, 1994

[54] PHYSIOLOGICALLY-CALIBRATED RATE ADAPTIVE, DUAL CHAMBER PACEMAKER

[75] Inventors: Peter A. Crosby, Greenwood Village; John R. Hamilton, Littleton; Anthony J. Ujhazy, Denver, all of Colo.

[73] Assignee: Telectronics Pacing Systems, Inc., Englewood, Colo.

[21] Appl. No.: 176

[22] Filed: Jan. 4, 1993

[51] Int. Cl.⁵ .............................. A61N 1/365
[52] U.S. Cl. ........................... 607/17; 607/18
[58] Field of Search ............ 607/17, 18, 19, 25

[56] References Cited

U.S. PATENT DOCUMENTS

| | | | |
|---|---|---|---|
| 4,228,803 | 10/1980 | Richards | 607/9 |
| 4,692,719 | 9/1987 | Whigham | 607/5 |
| 4,702,253 | 10/1987 | Nappholz et al. | 607/20 |
| 4,766,901 | 8/1988 | Callaghan | 607/26 |
| 4,856,522 | 8/1989 | Hansen | 607/17 |
| 4,901,725 | 2/1990 | Nappholz et al. | 607/17 |
| 4,903,701 | 2/1990 | Moore et al. | 607/22 |
| 5,085,215 | 2/1992 | Nappholz et al. | 607/17 |
| 5,226,414 | 7/1993 | Vandegriff et al. | 607/19 |

Primary Examiner—William E. Kamm
Assistant Examiner—George Manuel
Attorney, Agent, or Firm—Gottlieb, Rackman & Reisman

[57] ABSTRACT

A dual-chamber metabolic demand, rate adaptive pacemaker that automatically calibrates the correlation between a metabolic demand measurement and an appropriate metabolic demand pacing rate according to the true physiological needs of the body, as determined by a patient's sinus rate when the natural sinus rate is functioning in a reliable manner in the absence of cardiac arrhythmia.

50 Claims, 10 Drawing Sheets

PHYSIOLOGICALLY-CALIBRATED RATE ADAPTIVE, DUAL CHAMBER PACEMAKER

TECHNICAL FIELD

This invention relates to dual-chamber metabolic demand or rate adaptive (sometimes called rate-responsive) pacemakers and to a method of operation and use thereof. More particularly, this invention relates to a dual-chamber metabolic demand pacemaker which automatically calibrates the correlation between a metabolic demand measurement and an appropriate metabolic demand pacing rate.

BACKGROUND OF THE INVENTION

A rate-responsive pacemaker adjusts its pacing rate in accordance with the value of a measured parameter, called a rate control parameter (RCP). The RCP varies with the metabolic needs of the body and the value of the RCP measurement depends upon whether a patient is under stress, exercising or at rest. A rate-responsive pacemaker generally incorporates some parameter which relates the desired pacing rate as a function of the RCP. This parameter is a rate response factor (RRF), also called a "slope", which is programmed to select the degree of change in pacing rate that will occur for a given change in a sensed metabolic demand parameter (for example, minute volume). To program the RRF, a physician programs upper and lower pacing rate limits, then has a patient perform an exercise test to correctly ascertain the RRF.

In one example of a minute volume-based rate-responsive pacemaker (e.g. the pacemaker disclosed in U.S. Pat. No. 4,901,725, entitled "Minute Volume Rate-Responsive Pacemaker", issued Feb. 20, 1990 to T. A. Nappholz et al.), the pacer is implanted and programmed into an adaptive mode, in which the minute volume is sensed and calculated but the pacing rate does not respond to changes in minute volume. The patient is instructed to rest for at least an hour prior to the exercise test. During this time, the rate responsive sensing circuit adapts to the patient's individual respiratory impedance characteristics. Following the rest period, with the pacemaker remaining in the adaptive mode, the patient performs a near-maximal exercise test. The pacemaker calculates minute volume measurements for the rest and peak exercise conditions and, taking into account the programmed maximum and minimum pacing heart rates, the pacemaker and programmer determine a suggested optimal RRF value, which is displayed by the programmer. This is a recommended RRF value which the physician may program into the pacemaker. Similarly, other rate responsive pacemakers, such as those which base their rate adaptation upon activity, QT-interval, respiratory rate, central venous temperature, right ventricular pressure and other sensor measurements, determine a pacing rate dependent upon a programmable slope that correlates the sensed measurement to pacing rate.

One of the disadvantages of these rate-responsive pacemakers, which employ a programmable RRF function, is that the desired relationship between the measured rate control parameter and pacing rate does not remain constant for the life of a pacemaker or even from one programming to the next. For some rate-responsive pacemakers the RCP sensor is attached to a pacemaker lead or the RCP measurement is derived from an electrocardiogram signal which is sensed from the lead or leads. In either case, a change in lead position may cause an upward or downward shift in measured RCP values, leading to chronically elevated or lowered pacing rates. Furthermore, sensed RCP values vary with changes in sensor sensitivity or administration of drugs.

Another disadvantage of pacemakers with programmable RRF functions is that, in most cases, RRF initialization and programming procedures are complex and inefficient.

U.S. Pat. No. 4,856,522, entitled "Rate-Responsive, Distributed-Rate Pacemaker", issued Aug. 15, 1989 to J. C. Hansen, describes a rate-responsive heart pacer which modifies a rate response factor over time by arranging measured RCP values in a percentile ranking and mapping them into a percentile ranking of a desired rate distribution. By monitoring the RCP values over an extended time interval and developing a corresponding percentile ranking, the pacemaker automatically self-adapts to long-term changes in RCP measurements and insures that the desired rate distribution is obtained. One disadvantage of the Hansen pacer is that the range of pacing rates is determined by programming, so that the relationship between a particular RCP measurement and a pacing rate is based upon a prediction of what a proper relationship might be, rather than on the metabolic needs of a patient. A second disadvantage of the Hansen pacer is that it assumes that a patient will perform activities which exhibit a whole range of RCP values and require a whole range of heart rates on nearly a daily basis. Furthermore, the Hansen pacer will not respond rapidly to sudden changes in RCP sensitivity, such as those that result from a change in lead position. In addition, the Hansen pacer requires a relatively large amount of data storage memory for an implantable device. This disadvantage will become less critical as circuit technology evolves.

U.S. Pat. No. 5,085,215, entitled "Metabolic Demand Driven Rate-Responsive Pacemaker", issued to T. A. Nappholz et al. on Feb. 4, 1992, describes a dual-chamber rate-responsive pacemaker which senses two indicators of metabolic demand, the natural sinus rate and minute volume. This pacemaker continuously performs analysis of these two sensed parameters to determine whether a DDD or VVI pacing mode is most appropriate at a given time, at what rate pacing should be performed and, if a DDD mode is most appropriate, what time delay between an atrial heart beat and a ventricular pace should be set.

The primary object of the present invention is to provide for an analysis of natural sinus (atrial) rate and minute volume for a function not heretofore performed, namely, to determine an appropriate rate response factor based on the true metabolic needs of the body, as indicated by the natural atrial rate, but only under circumstances in which the natural atrial rate is functioning in a reliable manner.

It is another object of the present invention to provide for smoothing of the pacing rate when the pacemaker switches operations from one mode to another.

Further objects and advantages of the present invention will become apparent as the following description proceeds.

SUMMARY OF THE INVENTION

Briefly stated, and in accordance with one aspect of the present invention, there is provided a dual-chamber rate-responsive pacemaker which includes a pulse generator for generating ventricular pacing pulses, a cardiac electrical signal sensor to sense atrial heartbeats and a metabolic indicator sensor for measuring metabolic indicator values. The output of the cardiac electrical signal sensor is fed to an analyzer, such as a counter or averager, which determines an intrinsic atrial rate. The metabolic indicator sensor may measure any of the physiological parameters known in the art of cardiac pacing. Specific examples of metabolic indicator sensors employed by the pacemaker of the present invention include minute volume, paced depolarization integral, QT interval and oxygen saturation sensors, as well as any combination of these sensors in a multiple-sensor system. The pacemaker further includes a means for determining metabolic indicator rates as a function of the measured metabolic indicator sensor values and a predetermined rate response factor (RRF). The pacemaker includes a logic means for ascertaining whether sensed atrial heartbeats are occurring at rates which are either pathological or non-pathological, depending on the relative values of intrinsic atrial rate and the current metabolic indicator rate. Whether an atrial rate is determined to be pathological or non-pathological is based on the difference, over a range of rates, between the sensed atrial rate and the metabolic indicator rate, which is derived from the measured metabolic indicator sensor values. For example, a physician decides over which range of rates an intrinsic rhythm is non-pathological and programs the pacemaker accordingly.

In the context of the description of the present invention, the word "pathological" means a high intrinsic atrial rate, such as occurs in conditions of atrial fibrillation or atrial flutter. In other contexts, a low atrial rate is also considered to be pathological. In the discussion of the present invention, the meaning of the word "pathological" is not intended to encompass low atrial rates.

While the atrial-rate-pathology-ascertaining logic means is determining that the rate of atrial heartbeats is non-pathological, a memory stores at least one intrinsic atrial rate value, and at least one associated metabolic indicator value which is determined during the same cardiac cycle. The pacemaker may store an intrinsic atrial rate value which corresponds to the maximum detected atrial rate (the shortest atrial interval), or it may store the most recent atrial rate prior to detecting the occurrence of a pathological rhythm. Alternatively, the pacemaker may store a plurality of different intrinsic atrial rate samples and their cardiac-cycle-associated metabolic indicator values and, upon switching from the first to the second mode, perform a curve fitting or curve matching operation to determine a rate response factor.

The pacemaker further includes a controller to govern the operations of the pulse generator and the cardiac electrical signal sensor. The controller causes the pacemaker to operate normally in a DDDR (rate responsive DDD) mode, in which ventricular pacing pulses are generated in synchrony with atrial heartbeats, but to switch to a VVIR (rate responsive VVI) mode, in which ventricular pacing pulses are generated at a rate which is a function of the metabolic indicator rate and in which pulse timing is independent of the atrial heartbeats when the rates of atrial heartbeats are faster than the metabolic indicator rate and thus considered pathological. This controller, upon switching from the DDDR mode to the VVIR mode, concurrently updates the rate response factor as a function of the stored intrinsic atrial rates and metabolic indicator values. Thereafter, while the pacemaker is operating in the VVIR mode, the controller continuously updates the metabolic indicator rate, and therefore the pacing rate, as a function of the updated rate response factor and continuing metabolic indicator measurement values. If the intrinsic atrial rate is slower than the metabolic indicator rate, the controller then controls the pacemaker to operate in the DDDR mode.

In accordance with another aspect of the present invention, there is provided a dual-chamber rate-responsive pacemaker, which includes a pulse generator for generating atrial and ventricular pacing pulses, a cardiac electrical signal sensor to sense atrial and ventricular heartbeats and a metabolic indicator sensor for measuring metabolic indicator values. The pacemaker determines an intrinsic atrial rate using the output of the signal sensor and derives a metabolic indicator rate as a function of the metabolic indicator values and a predetermined and constantly updating rate response factor (RRF). The pacemaker compares the intrinsic atrial rate with the metabolic indicator rate to determine whether the natural atrial rhythm is pathological or non-pathological. If the natural rhythm is non-pathological, the pacemaker operates in an atrio-ventricular synchronous pacing (DDDR) mode, during which it measures and stores intrinsic atrial rate and metabolic indicator samples which are acquired during the same cardiac cycle. If the atrial rhythm becomes pathological, the pacemaker uses the stored atrial rate and metabolic indicator information to derive and update the rate response factor. Subsequently, the pacemaker begins to operate in a non-synchronous VVIR mode, in which the pacing rate is determined by the metabolic indicator value, in conjunction with the newly updated rate response factor.

BRIEF DESCRIPTION OF THE DRAWINGS

While the specification concludes with claims particularly pointing out and distinctly claiming the subject matter regarded as the invention herein, it is believed that the present invention will be more readily understood from the following description, taken in conjunction with the accompanying drawings, in which:

DETAILED DESCRIPTION OF THE INVENTION

Figure 1:
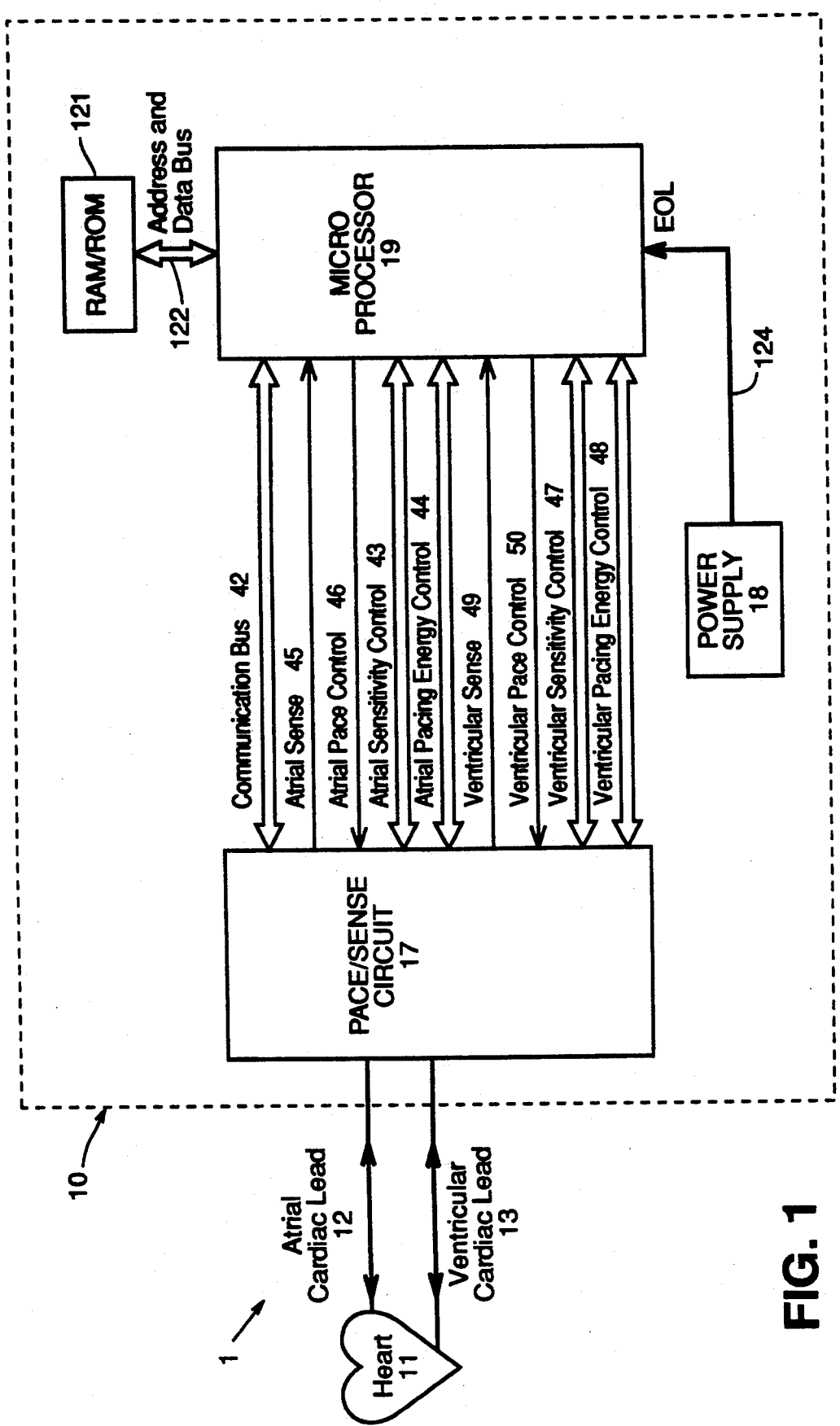
FIG. 1 is a block diagram of a rate-responsive, dual chamber pacemaker system in accordance with the present invention.

Referring to FIG. 1, there is depicted a block diagram of a pacemaker 1. Pacemaker 1 is designed to be implantable in a patient and includes a pulse module 10 and appropriate leads for connecting module 10 to a patient's heart 11. More particularly, pacemaker 1 will generally include an atrial cardiac lead 12 extending to the atrium of the patient's heart for sensing atrial signals and for the administration of pacing therapy to the atrium, and a ventricular cardiac lead 13 extending to the ventricle of the patient's heart for sensing ventricular signals and for the administration of pacing therapy to the ventricle. Pacemaker 1 generally also includes a pace/sense circuit 17 for the detection of analog signals representing cardiac electrical activity and for the delivery of pacing pulses to the heart; a microprocessor 19 which, in response to numerous inputs received from the pace/sense circuit 17, performs operations to generate different control and data outputs to the pace/sense circuit 17; and a power supply 18 for the provision of a reliable voltage level to pace/sense circuit 17 and microprocessor 19 by suitable electrical conductors (not shown).

Microprocessor 19 is connected to a random access memory/read only memory (RAM/ROM) unit 121 by an address and data bus 122. An end-of-life (EOL) signal line 124 is used to provide, to microprocessor 19, a logic signal indicative of the approach of battery failure in power supply 18. As more fully described below, microprocessor 19 and pace/sense circuit 17 are connected by a communication bus 42, an atrial sense line 45, an atrial pace control line 46, an atrial sensitivity control bus 43, an atrial pace energy control bus 44, a ventricular sense line 49, a ventricular pace control line 50, a ventricular sensitivity control bus 47, and a ventricular pace energy control bus 48.

Figure 2:
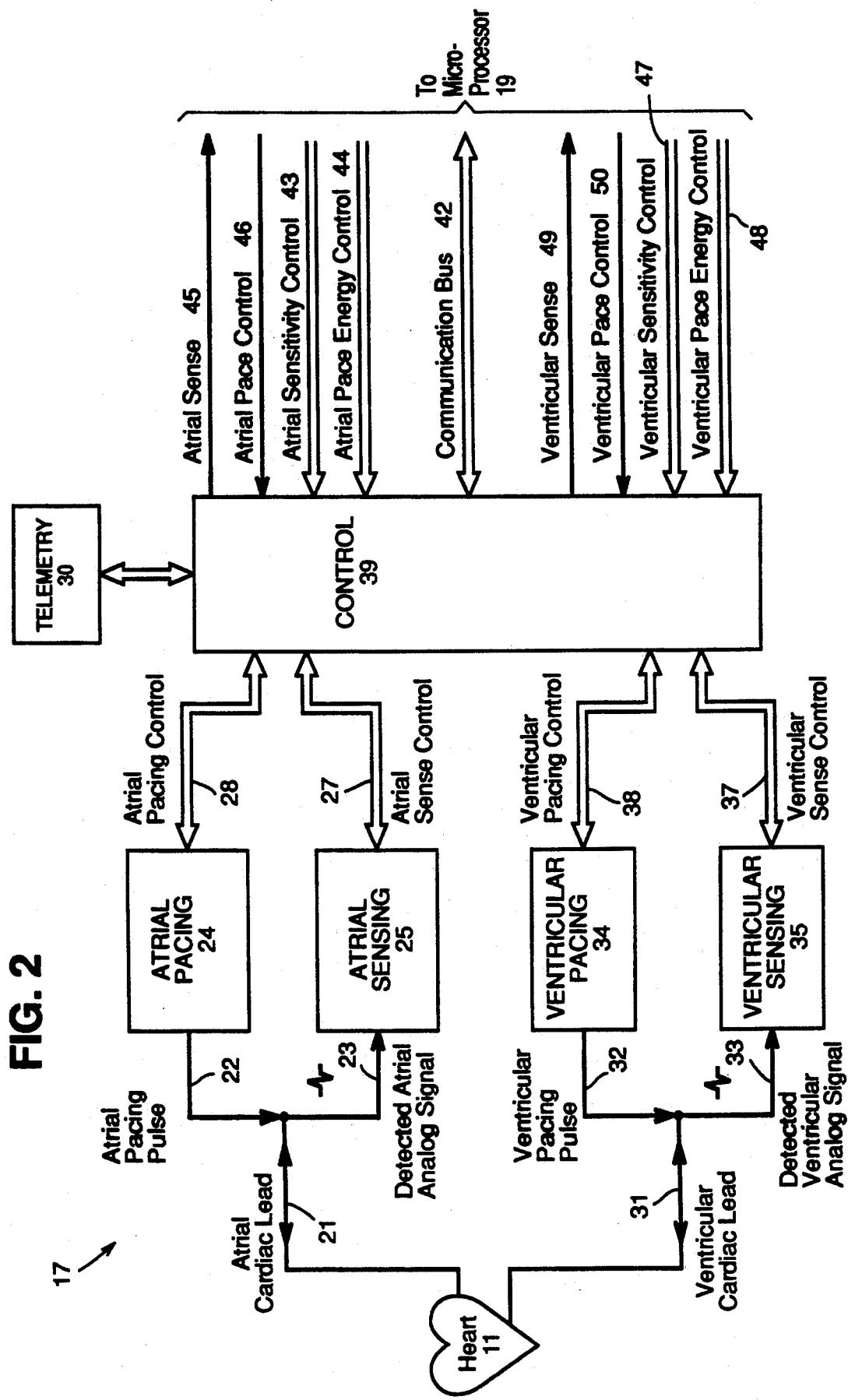
FIG. 2 is a block diagram of a pace/sense circuit utilized in the system of FIG. 1.

Referring to FIG. 2, pace/sense circuit 17 comprises circuitry for atrial pacing 24, ventricular pacing 34, atrial sensing 25, ventricular sensing 35, and telemetry 30. In addition, pace/sense circuit 17 includes a control block 39 which includes an interface to microprocessor 19.

In operation, sensing circuits 25 and 35 detect respective atrial and ventricular analog signals 23 and 33 from the heart 11 and convert the detected signals to digital signals. In addition, the sensing circuits 25 and 35 receive an input atrial sense control 27 and an input ventricular sense control 37, respectively, from the control block 39 which determines the sensitivity applied to the detection circuit. As more fully described below, a change in this sensitivity affects the voltage deviation required at the sensing electrode for a sense to be registered.

Atrial pacing circuit 24 receives from control block 39, via an atrial pacing control bus 28, an atrial pace control input and an atrial pacing energy control input. Similarly, ventricular pacing circuit 34 receives from control block 39, via a ventricular pacing control bus 38, a ventricular pace control input and a ventricular pacing energy control input. The atrial and ventricular pace control inputs determine the respective types of atrial and ventricular pacing to occur, while the atrial and ventricular pacing energy control inputs determine the respective magnitudes of the pulse energy.

Telemetry circuit 30 provides a bidirectional link between control block 39 of pace/sense circuit 17 and an external device such as a programmer. It allows data such as the operating parameters to be read from or altered in the implanted module 10.

Figure 3:
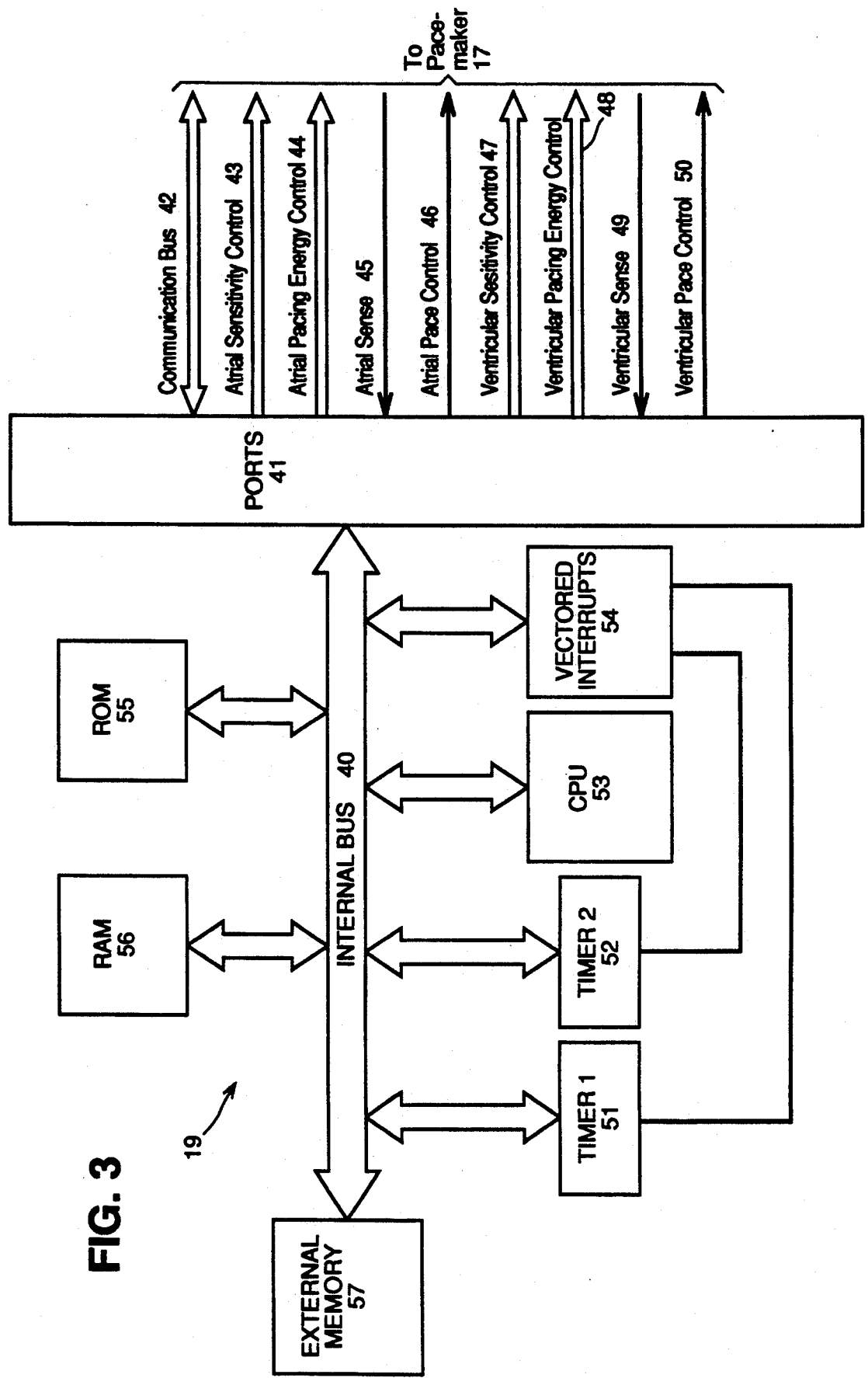
FIG. 3 is a block diagram of a microprocessor utilized in the system of FIG. 1.

Referring to FIG. 3, microprocessor 19 comprises two 16-bit timers 51 and 52, a CPU 53, a vectored interrupts block 54, a ROM 55, a RAM 56, an external memory 57, a ports block 41 and an internal communications bus 40. RAM 56 acts as a scratch pad and active memory during execution of the programs stored in ROM 55 and used by microprocessor 19. These programs include system supervisory programs, detection algorithms for detecting and confirming arrhythmias, and programming for implementing the logic flow diagram of FIGS. 6, 9 and 10, as well as storage programs for storing, in external memory 57, data concerning the functioning of module 10 and the electrogram provided by ventricular cardiac lead 13 (FIG. 1). Timers 51 and 52, and associated control software, implement some timing functions required by microprocessor 19 without resort entirely to software, thus reducing computational loads on and power dissipation by CPU 53.

Signals received from telemetry circuit 30 (FIG. 2) permit an external programmer (not shown) to change the operating parameters of pace/sense circuit 17 by supplying appropriate signals to control block 39. Communication bus 42 serves to provide signals indicative of such control to microprocessor 19.

Appropriate telemetry commands may cause telemetry circuit 30 to transmit data to the external programmer. Data stored is read out, by microprocessor 19, on to communication bus 42, through control block 39 in pace/sense circuit 17, and into telemetry circuit 30 for transmission to the external programmer by a transmitter in telemetry circuit 30.

Microprocessor 19 receives status and/or control inputs from pace/sense circuit 17, such as the sense signals on sense lines 45 and 49. It performs operations, including arrhythmia detection, and produces outputs, such as the atrial pace control on line 46 and the ventricular pace control on line 50, which determine the type of pacing that is to take place. Other control outputs generated by microprocessor 19 include the atrial and ventricular pacing energy controls on buses 44 and 48, respectively, which determine the magnitude of the pulse energy, and the atrial and ventricular sensitivity controls on buses 43 and 47, respectively, which determine the sensitivity settings of the sensing circuits.

A metabolic sensor system suitable for the present invention may be made up of one or more known sensors, either solely or in combination with other sensors, including but not limited to minute volume ie, depolarization gradient, QT-interval, oxygen saturation, pH, central venous blood temperature, right ventricular pressure, stoke volume, systolic time intervals, respiration rate and ultrasonic or pressure monitoring of cardiac output. The pacemaker 1 of the present invention will function properly using any metabolic indicator system, so long as that system is able to reliably relate the sensed parameter to a metabolic demand pacing rate.

U.S. Pat. No. 4,766,901, to F. J. Callaghan, dated Aug. 30, 1988, and entitled "Rate Responsive Pacing System Using the Integrated Evoked Potential," refers to the operation of a rate-responsive pacing system using an integrated evoked potential for a metabolic demand pacing rate indicator. U.S. Pat. No. 4,702,253 to T. J. Nappholz et al. dated Oct. 27, 1987, and entitled "Metabolic-Demand Pacemaker and Method of Using the Same to Determine Minute Volume," discloses a rate-responsive pacer describing a second metabolic demand pacing rate indicator, respiratory minute volume, as the rate control parameter. U.S. Pat. No. 4,692,719 to R. H. Whigham, dated Sep. 8, 1987, and entitled "Combined Pacemaker Delta Modulator and Bandpass Filter," describes electronic circuitry capable of performing electrocardiogram sensing for analyzing intrinsic and evoked potential cardiac signals. Improved pacers are disclosed in the copending application of F. J. Callaghan et al., Application Ser. No. 613,466, entitled "Rate-Responsive Pacemaker with Closed-Loop Control", filed on Nov. 7, 1990, and in the aforesaid U.S. Pat. No. 4,901,725 to T. J. Nappholz et al. The disclosures of the above-mentioned patents and application are hereby incorporated by reference.

The pacemaker of the present invention may also incorporate a QT interval sensor, such as that disclosed by A. F. Rickards in U.S. Pat. No. 4,228,803, entitled "Physiologically Adaptive Cardiac Pacemaker", issued Oct. 21, 1980. In another embodiment, the pacemaker of the present invention may also incorporate an oxygen saturation sensor, for example that disclosed by A. A. Moore et al. in U.S. Pat. No. 4,903,701, entitled "Oxygen Sensing Pacemaker", issued Feb. 27, 1990.

Figure 4:
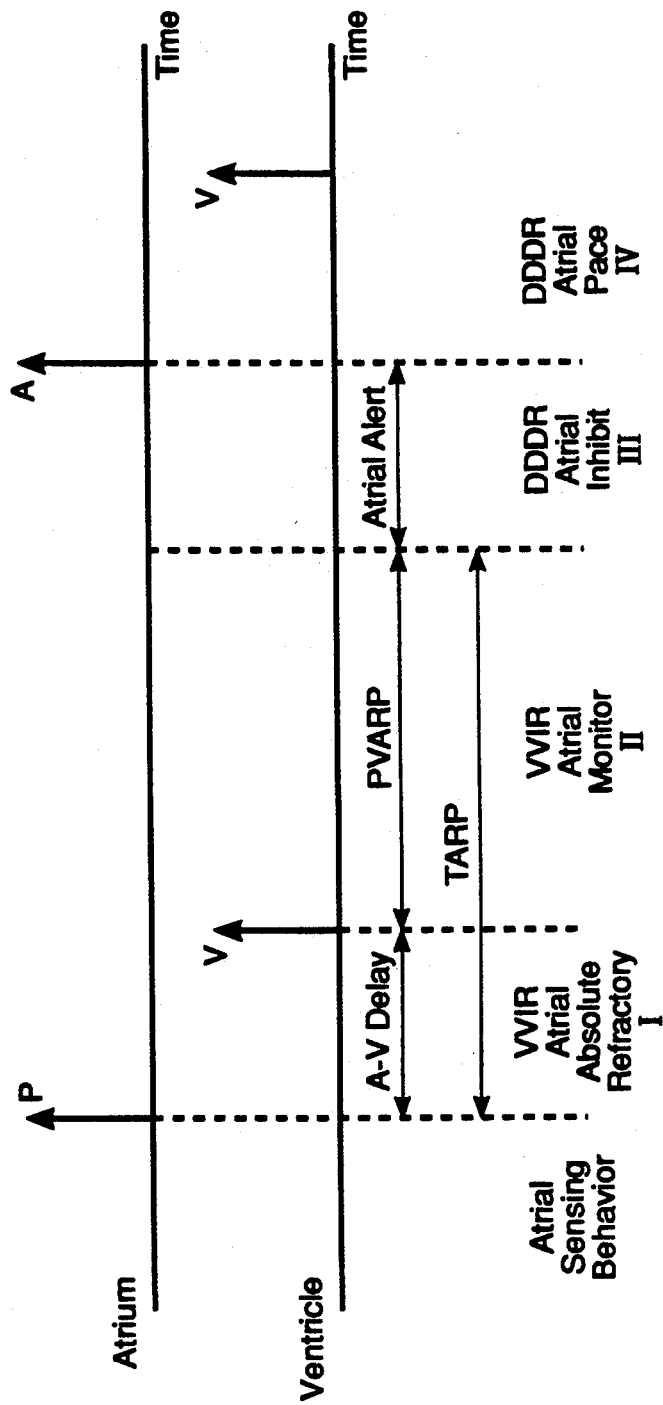
FIG. 4 is a timing diagram of a cardiac cycle and its associated timed intervals which shows the response of the pacemaker to cardiac events occurring in different timed intervals.
Figure 5A:
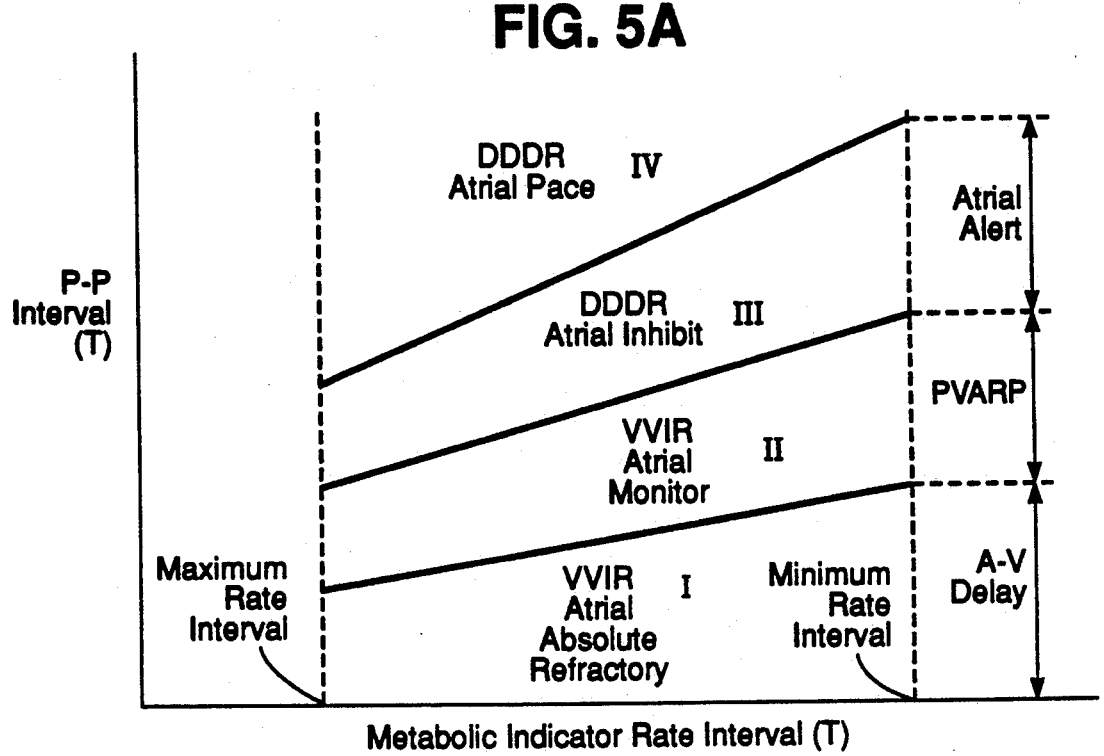
FIGS. 5A and 5B are graphs relating the rate of natural atrial sensing to the metabolic indicator rate parameter in terms of cardiac cycle time and rate, respectively, to indicate how the pacemaker responds to a natural atrial depolarization as a function of metabolic indicator rate.
Figure 5B:
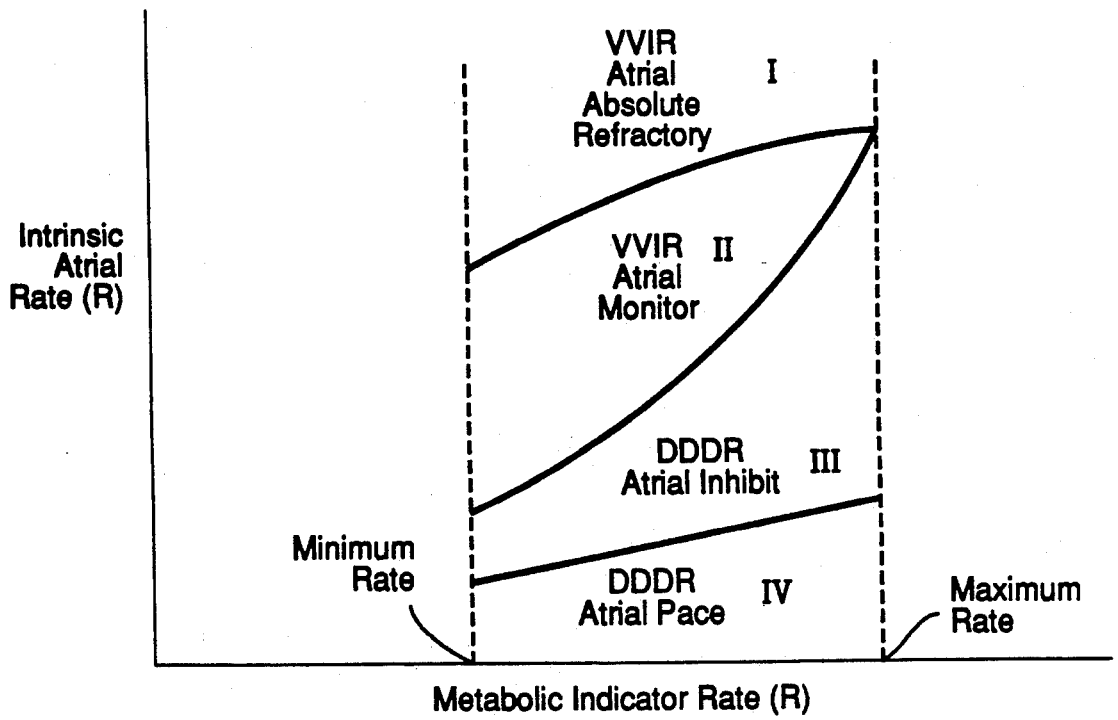

The timing diagram in FIG. 4 and the graphs of FIGS. 5A and 5B illustrate the manner of operation of the invention (FIG. 5B is derived from FIG. 5A simply by converting time interval values to the corresponding rates). In the preferred embodiment of the present invention, the pacemaker 1 first determines the metabolic indicator rate by ascertaining it from measurements of respiratory minute volume (MIRmv) in the manner described in the aforesaid T. J. Nappholz et. al. U.S. Pat. No. 4,901,725. Other embodiments of the pacemaker 1 may derive a metabolic indicator rate from another parameter, such as integrated evoked potential (MIRep), as described in the aforesaid F. J. Callaghan U.S. Pat. No. 4,766,901. Still additional embodiments of the pacemaker 1 may derive two or more metabolic indicator rates, such as MIRmv and MIRep.

Where two metabolic indicator rates are derived, the pacemaker 1 may limit MIRep and MIRmv to predetermined maximum values, with MIRep limited to a lower rate than MIRmv. The pacemaker 1 then mutually compares current MIRmv and MIRep values and sets the selected metabolic indicator rate (MIR) to the maximum of the two, for each cardiac cycle, and derives operational rates or intervals from such selected MIR. In general, it is desirable that multiple MIR sensors be employed and that they function independently, with one MIR sensor responding quickly to increases in metabolic demand, and a second MIR sensor responding in a slower, more stable manner. MIRep is the parameter of rapid response and MIRmv offers stability.

For a given implementation, the metabolic indicator sensor and rate-determining system may supply the pacemaker 1 with either the metabolic indicator rate (MIR) or its reciprocal, the metabolic indicator rate interval (MIRI). From either of these MIR parameter values, the pacer determines necessary rates or intervals. The pacer uses the MIR parameter to determine the minimum cardiac pacing rate, the maximum atrial tracking rate, and an A-V Delay for maintaining synchrony in the heart chambers.

The minimum cardiac pacing rate (minimum Rate in FIG. 5B) is the overall DDDR pacing rate, the lower limit of the cardiac rate when atrial activity is slow or absent. In the illustrative embodiment of the invention, the pacer sets the minimum cardiac pacing rate equal to the metabolic indicator rate MIRmv or MIRep.

The maximum atrial tracking rate (Maximum Rate in FIG. 5B) is the highest intrinsic atrial rate for which the ventricle is paced in synchrony with natural atrial activity. The pacer sets the maximum atrial tracking rate to a rate proportional to but higher than the MIR to allow sinus node tracking during exercise or stress. The relationship for determining maximum atrial tracking rate from the metabolic indicator rate is based on a clinical evaluation of the particular metabolic indicator method, and on how the derived MIR relates to the upper limit on pacing rate for an exercising patient. By basing the maximum atrial tracking rate on the MIR, when the patient exercises the metabolic indicator rate increases and this elevates the maximum atrial tracking rate. In turn, as the sinus rate increases with exercise, it is less likely to exceed the maximum atrial tracking rate and the pacemaker 1 can remain in the A-V synchronous mode.

The pacemaker 1 thus uses the metabolic indicator rate to set a maximum atrial tracking rate, the highest intrinsic atrial rate for which the pacemaker 1 will pace the ventricle in synchrony with the atrium. When the intrinsic atrial rate is slower than the maximum atrial tracking rate but is faster than the minimum cardiac pacing rate (Minimum Rate in FIG. 5B), sensed P waves (natural or intrinsic atrial heartbeats) fall within the Atrial Alert interval (FIGS. 4 and 5A) and the effective pacing rate is under the control of the heart's sinus node. Atrial pacing pulses A are inhibited and ventricular pacing pulses V will take place only if the heart's A-V conduction is not functioning properly, following the delay of a predetermined A-V Delay interval. While the pacemaker 1 is operating in this manner, an atrial heartbeat P triggers an A-V Delay interval timer, as in standard DDD pacing, but with the metabolic indicator rate automatically and continuously determining both the duration of the A-V Delay and the cardiac cycle length (see U.S. Pat. No. 5,085,215 for full disclosure of this operation). Pacing in these circumstances may be called a DDDR atrial inhibit mode because pacing is A-V synchronous with timely sensing of an R wave (a natural ventricular heartbeat) inhibiting ventricular pacing. Only the overall minimum pacing rate is determined by the metabolic sensor. Any intrinsic atrial rate higher then the metabolic indicator rate but lower than the maximum atrial tracking rate is set by the heart's sinus node. This type of operation is illustrated by region III in FIGS. 4, 5A and 5B.

The metabolic indicator rate takes control only when the intrinsic atrial rate is too low or too high. If the intrinsic atrial rate is too low, causing a timeout of an atrial rate timer, the Atrial Alert interval shown in FIG.

4, the pacemaker 1 stimulates the atrium with a pacing pulse A at the metabolic indicator rate and stimulates the ventricle with a ventricular pacing pulse V after an A-V Delay interval, unless natural ventricular activity inhibits pacing (see region IV in FIGS. 4, 5A and 5B.

If the intrinsic atrial rate is faster than the maximum atrial tracking rate, the sinus rate is too high and the pacemaker 1 senses a P wave during a post ventricular atrial refractory period (PVARP), as shown in region II of FIG. 4. The pacemaker 1 responds by ignoring the P wave, for purposes of triggering ventricular pulse generation V. The pacemaker 1 switches pacing mode from DDDR to VVIR. VVIR pacing mode is the standard VVI pacing mode, but having a pacing rate determined according to measurements of a metabolic sensor. If the pacemaker 1 senses a P wave in region I, during the A-V Delay, it ignores the P wave for all control purposes. The pacemaker 1 switches operation from the DDDR mode to the VVIR mode when the intrinsic atrial rate is faster than the maximum atrial tracking rate. In the illustrative embodiment of the invention, the pacemaker 1 switches to the VVIR mode when P waves fall within the PVARP interval for a predetermined number of consecutive cardiac cycles.

While operating in either the VVIR or DDDR modes, the pacemaker 1 measures the metabolic indicator rate and, accordingly, updates a total atrial refractory period (TARP), the time interval that corresponds in a reciprocal relationship to the maximum atrial tracking rate. Also, while operating in any mode, the pacemaker 1 monitors atrial activity to detect atrial rate slowing and determine when to switch modes, from DDDR to VVIR mode or back to DDDR mode. While functioning in the DDDR mode, the pacemaker 1 senses P waves both to trigger ventricular pacing and to determine whether the intrinsic rate is too fast, in which case the pacing mode is switched to VVIR mode. In the VVIR mode, the pacemaker 1 continues to sense P waves to determine whether the intrinsic atrial rate continues to be faster than the maximum atrial tracking rate. The pacemaker 1 senses P waves and determines whether the P-P interval is longer or shorter than the TARP. In this mode, the pacemaker 1 only senses P waves for the purpose of determining whether it can switch back to DDDR mode.

An atrial rate monitor performs analysis of P wave timing to determine whether the intrinsic atrial rate is sufficiently fast or slow to warrant changing operating modes. The atrial rate monitor counts the number of cardiac cycles to accumulate a record of P waves occurring inside and outside of the TARP in recent cycles. If a predefined proportion of cardiac cycles have P waves falling within the TARP, the intrinsic atrial rate is considered fast and switching from DDDR mode to VVIR mode is appropriate. Conversely, if another predefined proportion of cardiac cycles have P waves falling outside the TARP, the intrinsic atrial rate is considered slow and switching from VVIR to DDDR mode is warranted. For example, the atrial rate monitor may include a counter, which increments to a maximum of three whenever a P—P interval is shorter than the TARP and decrements to a minimum of zero when a P—P interval is longer than the TARP.

The pacemaker 1 initiates the VVIR mode when operating in the DDDR mode upon sensing a preset number of consecutive cardiac cycles in which P valves occur within the TARP. The pacemaker 1 increments the atrial rate monitor counter from zero to one upon the first sensed P wave during TARP and increments the monitor for each succeeding P wave sensed during TARP. If the pacemaker 1 senses P waves in TARP for the preset number of consecutive cardiac cycles, it switches to VVIR pacing mode and then operates in the VVIR mode as long as the count is greater than zero. For instance, if two cardiac cycles with premature P waves are required to cause the pacemaker 1 to function in VVIR mode and two consecutive premature P waves are followed by two P waves separated by intervals longer than TARP, the pacemaker 1 decrements the atrial rate monitor counter back to zero and returns to operating in the DDDR mode in the following cardiac cycle. However, if several P waves occur at intervals shorter than TARP or, more accurately, if more P-P intervals are shorter than TARP than are longer, the pacemaker 1 increments the atrial rate monitor counter up to a maximum of three. This requires a sequence during which there are three more P—P intervals longer than the TARP than P—P intervals shorter than TARP before the pacemaker 1 decrements the counter back to zero and switches back to the DDDR mode.

In this manner, the pacemaker 1 distinguishes between isolated premature atrial depolarizations and atrial tachycardia. For an isolated premature P wave the pacemaker 1 continues to operate in the DDDR mode without interruption. Infrequent consecutive premature P waves cause the ventricle to perform asynchronously with respect to the atrium for only a few cycles. In the case of atrial tachycardia, the pacemaker 1 will maintain VVIR pacing, requiring greater assurance of termination of the tachycardia episode before switching back to the DDDR operating mode.

Figure 6:
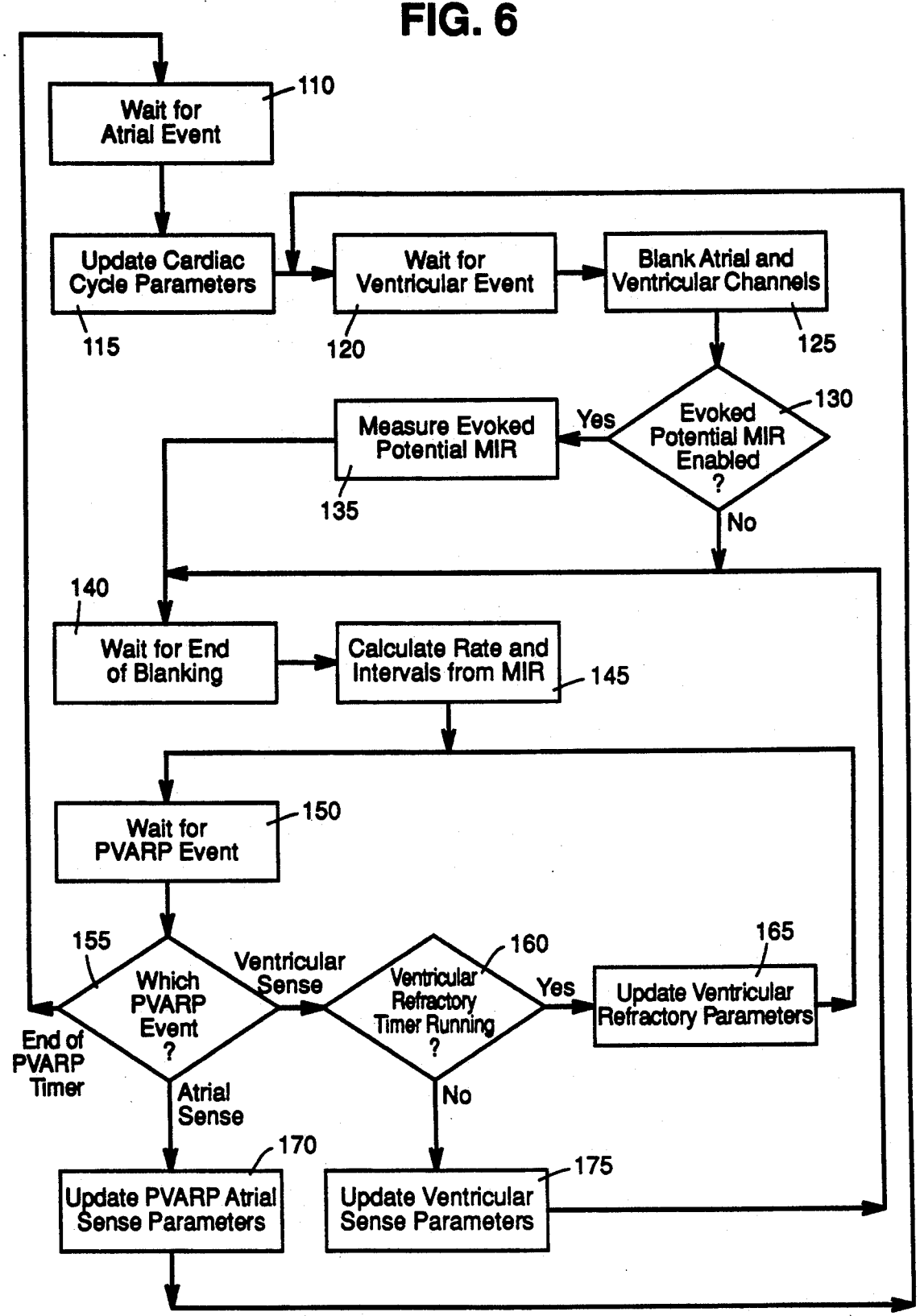
FIG. 6 is a flow diagram illustrating timing, cardiac polarization event detection, and operations performed in the illustrative embodiment of the invention.

FIG. 6 is a flow diagram showing control operations performed by the microprocessor 19 within pacemaker 1 (of FIG. 1) as time proceeds within a single cardiac cycle. The microprocessor 19 continuously repeats the cycle. The first block 110 represents the Atrial Alert wait state, which is illustrated in the timing diagrams of FIGS. 4 and 5A. Here the microprocessor 19 waits for either an ATRIAL SENSE signal or the time-out of the atrial timer, (one of Timers TIMER 1 51 or TIMER 2 52 of FIG. 3), defining the end of one cardiac cycle and the beginning of the next. When the pacemaker 1 is functioning in DDDR mode, it is controlled by an atrial rate monitor (ARM, not shown) routine, which is performed by the microprocessor 19 of FIG. 1, and by a counter of consecutive P waves sensed during PVARP (neither of which operations is shown but both of which operations are performed by the microprocessor 19 of FIG. I and are described in detail hereinafter in a discussion of block 145). During such DDR mode functioning, the microprocessor 19 generates an atrial stimulus on time-out of the atrial timer in the wait-for-atrial-event block 110. It is while the system is in this block that the microprocessor 19 controls VVIR or DDDR operation by determining whether to generate an atrial stimulus.

The illustrative microprocessor 19 uses atrial event timing as a basis for timing other events in the cardiac cycle. Atrial-based timing allows implementation of the automatic A-V Delay feature of this invention more easily than an implementation which maintains rate according to ventricular-based timing (although the latter is not excluded). Most other dual chamber pacemakers use a constant ventricular-to-atrial (V-A) interval approach. The microprocessor 19 of this invention sets the cardiac rate according to the atrial-to-atrial (A—A) interval. The microprocessor 19 reverts to a rate defined by the V-A interval only after a premature ventricular contraction (PVC) which causes a ventricular R wave sensing to occur before pacing or sensing occurs in the atrium within the cardiac cycle. The reason for reverting to a rate defined by the V-A interval is that maintaining the A—A interval timing under this condition would cause an excessively fast ventricular pacing rate. Otherwise, the microprocessor 19 adjusts the A-V Delay and the V-A interval follows accordingly to maintain a P wave to atrial pacing (P-A) or A—A interval correlated with the metabolic indicator rate, regardless of variations in atrial-to-ventricular event timing.

Following an atrial event (sense or pace), the microprocessor 19 updates cardiac cycle control parameters, enables timers and sensing where appropriate in the atrium and ventricle, and processes the atrial rate monitor (ARM) and the retrograde monitor in update-cardiac-cycle-parameters block 115. How the microprocessor 19 controls cardiac cycle parameters depends on whether the event ending the cardiac cycle was ATRIAL SENSE or an atrial timer time-out and, for either of these events, whether the pacemaker 1 is operating in an A-V synchronous dual-chamber manner or temporarily in the VVIR mode in response to atrial tachycardia or retrograde conduction. In addition, the microprocessor 19 performs timing, sensing, data logging, atrial rate monitor, and retrograde monitor operations. During the update-cardiac-cycle-control parameters block 115, the microprocessor 19 also performs an automatic rate response factor (RRF) function of the present invention that is hereinafter discussed in conjunction with FIG. 9, and a rate smoothing operation, which is examined with relation to FIG. 10.

In update-cardiac-cycle-parameters block 115, the microprocessor 19 first updates the cardiac cycle interval data log by setting the current P wave to P wave (P—P) interval log to either: (1) the time loaded into the atrial timer at the time of the atrial event in the previous cardiac cycle if the current atrial event is atrial timer timeout, or (2) in the case of ATRIAL SENSE, the time in (1) reduced by the time remaining in the atrial timer.

The microprocessor 19 now, in update-cardiac-cycle-parameters block 115, services the atrial rate monitor (ARM, not shown). The ARM monitors the timing and recent history of cardiac cycles depending on whether the intrinsic atrial rate for a cycle is faster or slower than the maximum atrial tracking rate. If the pacemaker 1 is operating temporarily in the VVIR mode in response to an atrial rate faster than the maximum atrial tracking rate and the atrial rate begins to slow below that rate, the ARM acts in a controlled manner to delay the enabling of atrial pacing and sensing and synchronizing the heart chambers to pace in the DDDR mode. The amount of delay depends on how long the high atrial rate has prevailed. ARM informational parameters may include combinations of one or more of: high atrial rate counters, and history buffers expressing which of the last cardiac cycles had high and low rates. Linear and nonlinear control methods may use the informational parameters to time the recovery from high atrial rates. The illustrative embodiment of the invention uses a single counter, the ARM counter (not shown), which the microprocessor 19 increments for atrial tachycardia rates and decrements for slower atrial rates. At this point in the control flow, the microprocessor 19 decrements the ARM counter by one (unless it is already at the minimum of zero). The reason for this is that the branch to block 110, which precedes block 115, is from a logic block 155 in which the microprocessor 19 determines that the P—P interval is longer than the TARP. If the ARM counter reaches a minimum of zero, the microprocessor 19 will change modes from temporary VVIR to DDDR, but this will occur in an operation later in the cardiac cycle. The microprocessor 19 increments or decrements the ARM counter for every sensed P wave and atrial pace delivery regardless of the current operating mode of pacemaker 1.

The microprocessor 19 begins timing the next A—A interval by initializing the atrial timer to the interval specified by the metabolic indicator rate (MIR). This interval, in milliseconds, is 60,000 divided by the MIR (in beats per minute). Generally, the microprocessor 19 sets the A—A interval timer to the interval set by the MIR. However, in circumstances in which the microprocessor 19 is changing operation between the VVIR and the DDDR modes, it may be appropriate for the microprocessor 19 to set an A—A interval value different from that consistent with the MIR. For example, when switching from the DDDR mode where the rate has been driven by a high intrinsic atrial rate to a VVIR mode at the MIR, gradually ramping down the rate from the intrinsic atrial rate to the MIR is a possibility. Likewise, when changing from the VVIR to the DDDR mode, the microprocessor 19 may gradually reduce the A—A interval from that set from the MIR to one consistent with the sensed intrinsic atrial rate.

If the pacemaker 1 is operating in the DDDR mode, it generates a stimulating pulse (APACE). Also after atrial timer time-out, the microprocessor 19 divides the A-V Delay interval into two subintervals timed by a subinterval timer, performed by either TIMER 1 51 or TIMER 2 52 of FIG. 3. In the first blanking interval, typically 80 milliseconds, the microprocessor 19 disables ATRIAL SENSE and VSENSE for long enough to prevent sensing of the atrial pacing pulse, its artifact, and any evoked potential. After the subinterval timer time-out, the microprocessor 19 resets the subinterval timer to an interval which, when added to the first blanking interval, sets the automatic A-V Delay interval. The microprocessor 19 enables VSENSE at this time to allow intrinsic ventricular R waves to inhibit VPACE, while ATRIAL SENSE remains disabled during the entire A-V Delay interval.

If the event ending the cardiac cycle was ATRIAL SENSE and the pacemaker 1 is operating in the DDDR mode, it sets the A-V Delay interval timer offset by a latency factor. The A-V Delay value is based on the time between APACE and VSENSE for normal atrioventricular conduction for the patient. The microprocessor 19 modifies the A-V Delay by a latency factor, as is known in the art, to account for differences in conduction time between paced atrial activity (ATRIAL PACE) and intrinsic atrial activity (ATRIAL SENSE). The value of the latency factor may vary depending on such conditions as location of the leads, atrial sense threshold, and atrial sensitivity. At the subsequent A-V Delay timeout, the pacemaker 1 will stimulate the ventricle (VPACE), unless pacing is inhibited by VSENSE.

A retrograde monitor (not shown) operates by counting consecutive cardiac cycles in which sensed atrial events occur during the PVARP interval while a running average (over about four cycles) of the P—P interval log corresponds to a rate slower than the maximum atrial tracking rate. An ATRIAL SENSE occurring subsequent to the PVARP interval or an atrial cycle time-out breaks any string of consecutive retrograde cycles. At this point in the control flow, the microprocessor 19 resets the retrograde monitor to zero because the consecutive count has been broken.

Wait-for-ventricular-event block 120 represents the ventricular alert wait state. Here the microprocessor 19 waits for either VSENSE or the time-out of the A-V Delay interval. Upon either event, in the blanking control operation of blank-atrial-and-ventricular-channels block 125, the pacemaker disables ATRIAL SENSE and VSENSE and times a blanking interval corresponding to the atrial absolute refractory period (AARP). Within the AARP, natural P waves cannot physiologically occur, so the pacemaker blanks to avoid atrial sensing of such extraneous events as ventricular stimulation, stimulus artifact, and evoked potential. If the ventricular event was time-out of the A-V Delay timer rather than VSENSE, then the pacemaker 1 generates a stimulating pulse (VPACE).

If the microprocessor 19 metabolic indicator system uses evoked potential sensing, determined in evoked-potential-MIR-enabled? logic block 130, the microprocessor 19 performs an evoked potential MIR measurement and rate determination in block 135. (The illustrative embodiment of the invention includes a mechanism for individually enabling or disabling each metabolic sensor within the MIR system, using telemetry).

The microprocessor 19 waits for the end of blanking in block 140. It is in calculate-rate-and-intervals-from-MIR block 145 that the MIR is used to calculate the new A-V Delay and PVARP values as well as the new cycle length (A—A interval). Also, PVARP timing begins. Since the microprocessor 19 traverses this flow path during every cardiac cycle, in the illustrative embodiment of the invention important rate and interval control operations are performed during the rate and interval calculations of block 145.

The next operation performed in the rate and interval calculation block 145 of FIG. 6 is determination of the maximum atrial tracking rate from the A-V Delay and the PVARP. The maximum atrial tracking rate is the inverse of the total atrial refractory period TARP, which is the sum of the A-V Delay and the PVARP. Because the microprocessor 19 automatically determines both the A-V Delay and the PVARP as functions of metabolic indicator rate, maximum atrial tracking rate is likewise a function of MIR. The maximum atrial tracking rate defines the boundary between DDDR and VVIRtype pacing in the illustrative embodiment of the invention.

If the microprocessor 19 must sense P waves during PVARP for two consecutive cardiac cycles while functioning in DDDR mode to trigger the change to VVIR mode, the microprocessor 19 will sustain A-V synchronous pacing in response to a single premature atrial contraction. If the pacemaker 1 begins pacing temporarily in the VVIR mode because of two premature atrial contractions, the atrial rate monitor ARM counter only has to decrement in block 115 from two to zero before restoring DDDR mode operations in the following cardiac cycle. If the pacemaker 1 performs in the VVIR mode due to atrial tachycardia, the ARM counter will increment (in block 170, to be described below) to a maximum value of three. The ARM counter must decrement for at least three cycles after the tachycardia terminates before the microprocessor 19 can restore atrial pacing. But there is an additional mechanism for resetting the ARM counter to zero in order to rapidly restore atrial pacing. In block 145, a two-second timer determines whether atrial sensing has not taken place for two seconds. In the absence of atrial sensing, there is no tachycardia and, therefore, no need to inhibit atrial pacing. Consequently the microprocessor 19 resets the ARM counter to zero.

In the final operation within the rate and interval calculation block 145, the microprocessor 19 prepares for atrial and ventricular refractory operations. In the atrium, the microprocessor 19 enables ATRIAL SENSE for sensing during the newly determined PVARP interval. The microprocessor 19 delays the ventricular blanking period (70 milliseconds beyond the 80-ms atrial blanking period) because VSENSE during the ventricular absolute refractory period is not a significant event with regard to cardiac physiology (any sensed signal must be noise).

The microprocessor 19 now waits for ATRIAL SENSE, VSENSE, and PVARP timer events during the wait-for-PVARP-event block 150. Logic blocks 155 and 160 determine control flow upon one of the three events. Time-out of the PVARP timer ends the PVARP, after which logic block 155 controls a branch to wait-for-atrial-event block 110; the Atrial Alert period always follows a PVARP time-out.

If the PVARP event is a ventricular sense, then in logic block 160 the microprocessor 19 makes a test to determine whether a ventricular refractory timer is running. As described above, initially the microprocessor 19 times a 70 millisecond absolute refractory interval. The microprocessor 19 ignores all ventricular sense events which occur during this interval. After this absolute refractory interval, the microprocessor 19 times a 150 millisecond relative refractory interval. An R wave sensed during the relative refractory interval restarts the 150-ms timer but otherwise has no effect (the R wave is treated as noise and is ignored). If the control flow for microprocessor 19 enters update-ventricular-refractory-parameters block 165 within the first 70 milliseconds of timing of the ventricular refractory timer, the microprocessor 19 ignores the ventricular sense event and returns to block 150 where the system again waits for a PVARP event. If the microprocessor 19 enters block 165 after a timeout of the absolute refractory period but before a time-out of the ventricular relative refractory timer (i.e., within 220 milliseconds of timing after the beginning of the PVARP interval), the pace restarts the timer and the system notes that relative refractory timing is in progress. Subsequent entries into block 165 do the same thing; in every case the microprocessor 19 returns control to block 150. If a ventricular sense event occurs when the timer has proceeded beyond 150 milliseconds in a relative refractory interval, either the original relative refractory interval or a restarted interval, it is an indication that a premature ventricular contraction has occurred, i.e., a ventricular beat during the PVARP but after the ventricular absolute and relative refractory periods.

The microprocessor 19 responds to such a premature ventricular contraction sensing in update-ventricular-senseparameters block 175 and then branches to the wait-for-end-of-blanking block 140. Atrial events should always precede ventricular events. Occurrence of a premature ventricular event, one that precedes the atrial event for that cardiac cycle, signifies the end of the cardiac cycle. The microprocessor 19 moves on to the next cardiac cycle by disabling ATRIAL SENSE and VSENSE in block 175 and then branching to block 140 since a ventricular event has just occurred. But there is one modification to the usual processing which is required. There is a timer running which times the A—A interval. This timer requires a new value. Instead of timing a full cycle from the last P valve or APACE, what is required is timing of the V-A interval from the R wave just sensed. The microprocessor 19 subtracts the A-V Delay from the total A—A cycle length (the time loaded into the A—A timer in block 115), and uses the resulting V-A interval to set the timer defining the time-out event ending block 110.

In the update-PVARP-atrial-sense-parameters block 170, the microprocessor 19 services ATRIAL SENSE events falling within the PVARP interval. First the microprocessor 19 measures the immediate P wave to P wave (P—P) interval by reducing the timer interval last loaded into the atrial timer by the time left in the atrial timer. The current instantaneous atrial timer value holds the time left in the atrial cycle because this timer is a down counter. The microprocessor 19 uses the latest P-P interval value to update the running P-P interval average which is required for retrograde monitor processing. The microprocessor 19 services the atrial rate monitor (ARM) by incrementing the ARM counter to a maximum of three since, in this instance, the P—P interval is shorter than the TARP. Also, the microprocessor 19 sets the A—A interval timer, the A-V Delay, and the blanking interval just as they are set in block 115.

The microprocessor 19 now processes the retrograde monitor in update-PVARP-atrial-sense-parameters block 170. The action of temporarily changing the operating mode from DDDR to VVIR creates the problem of a new form of pacer mediated tachycardia (PMT), Pacemaker-Mediated VVIR (PMVVIR). This phenomenon occurs when retrograde conduction during the VVIR mode causes a P wave to consistently fall in the PVARP.

The retrograde monitor detects and terminates retrograde (V-A) conduction. The first step toward detecting PMVVIR is defining it within the context of the present invention. The characterization of PMVVIR within a cardiac cycle is: (a) a P wave occurring within the PVARP, when (b) the P—P interval running average is larger than the maximum atrial tracking rate interval. The retrograde monitor in update-PVARP-atrial-sense-parameters block 170 detects PMVVIR by counting such events while the pacemaker 1 is functioning in VVIR mode in response to pathological atrial tachycardias. If a predefined number (five in the preferred embodiment of the invention) of consecutive retrograde cycles occur, the retrograde monitor classifies the phenomenon as PMVVIR and begins its reversion response.

The retrograde monitor terminates the PMVVIR retrograde conduction condition using a pace cycle extension procedure wherein the microprocessor 19 extends one cardiac cycle (A—A interval, timed by the atrial timer) by a predetermined amount (for example, 240 ms). This terminates the PMVVIR condition by restoring A-V synchrony. The microprocessor 19 makes a branch to block 120 to wait for a ventricular event; the actual A—A cycle extension occurs in the next loop where block 110 is extended. To insure that the microprocessor 19 reaches block 110 requires a branch during the next cycle from block 155 to block 110. To guarantee this branch, part of the retrograde monitor processing in block 170 includes setting a flag which causes both atrial and ventricular sense events to be ignored during the next cycle in block 155. The retrograde monitor processing also includes the step of setting the ARM counter to zero so that the DDDR mode of operation can resume upon the next entry into block 110.

Figure 7:
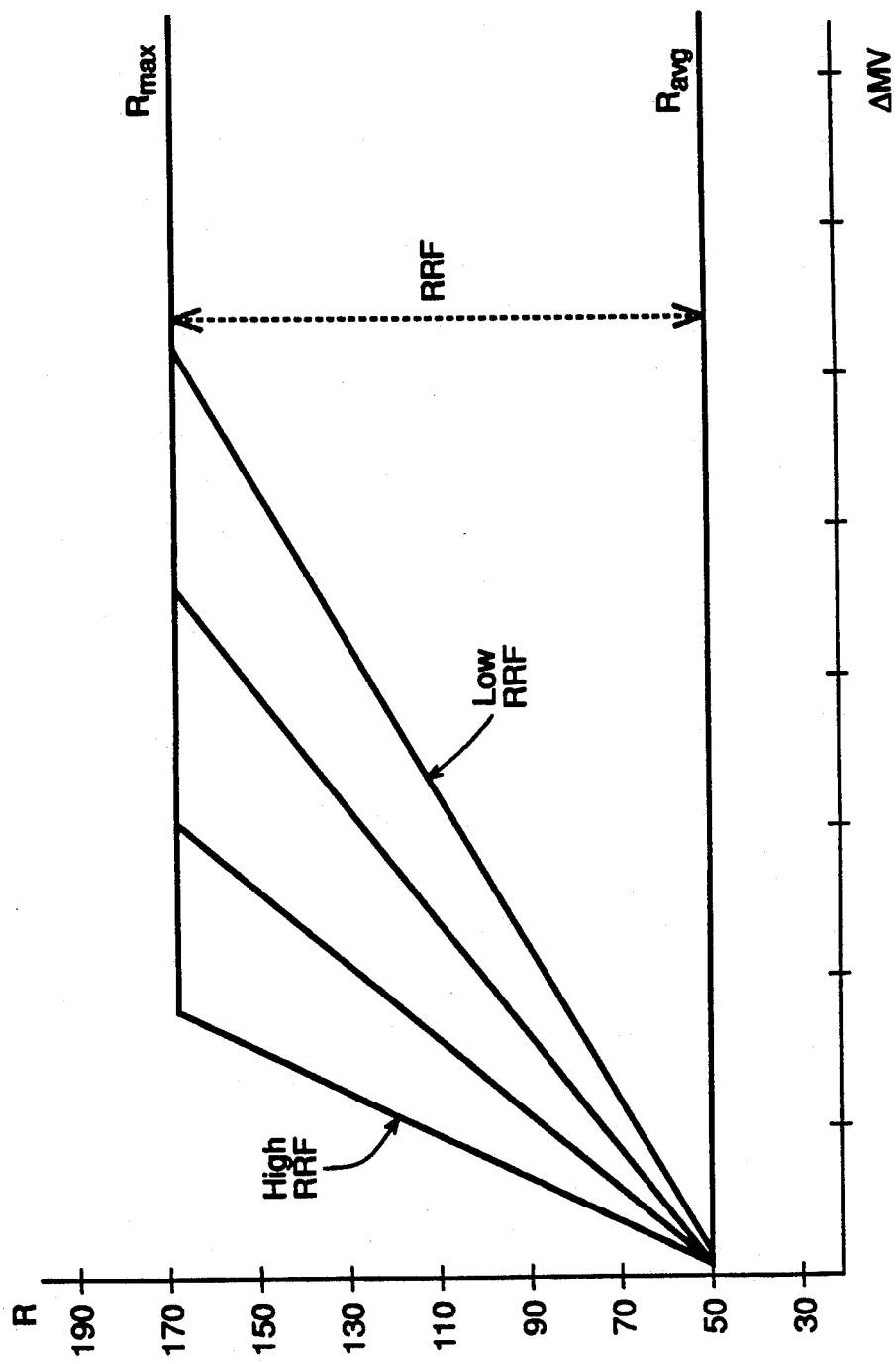
FIG. 7 is a graph which illustrates a plurality of single slope rate response factors (RRF) for a minute volume metabolic indicator sensor which sets the relationship between minute volume and pacing rate.
Figure 8:
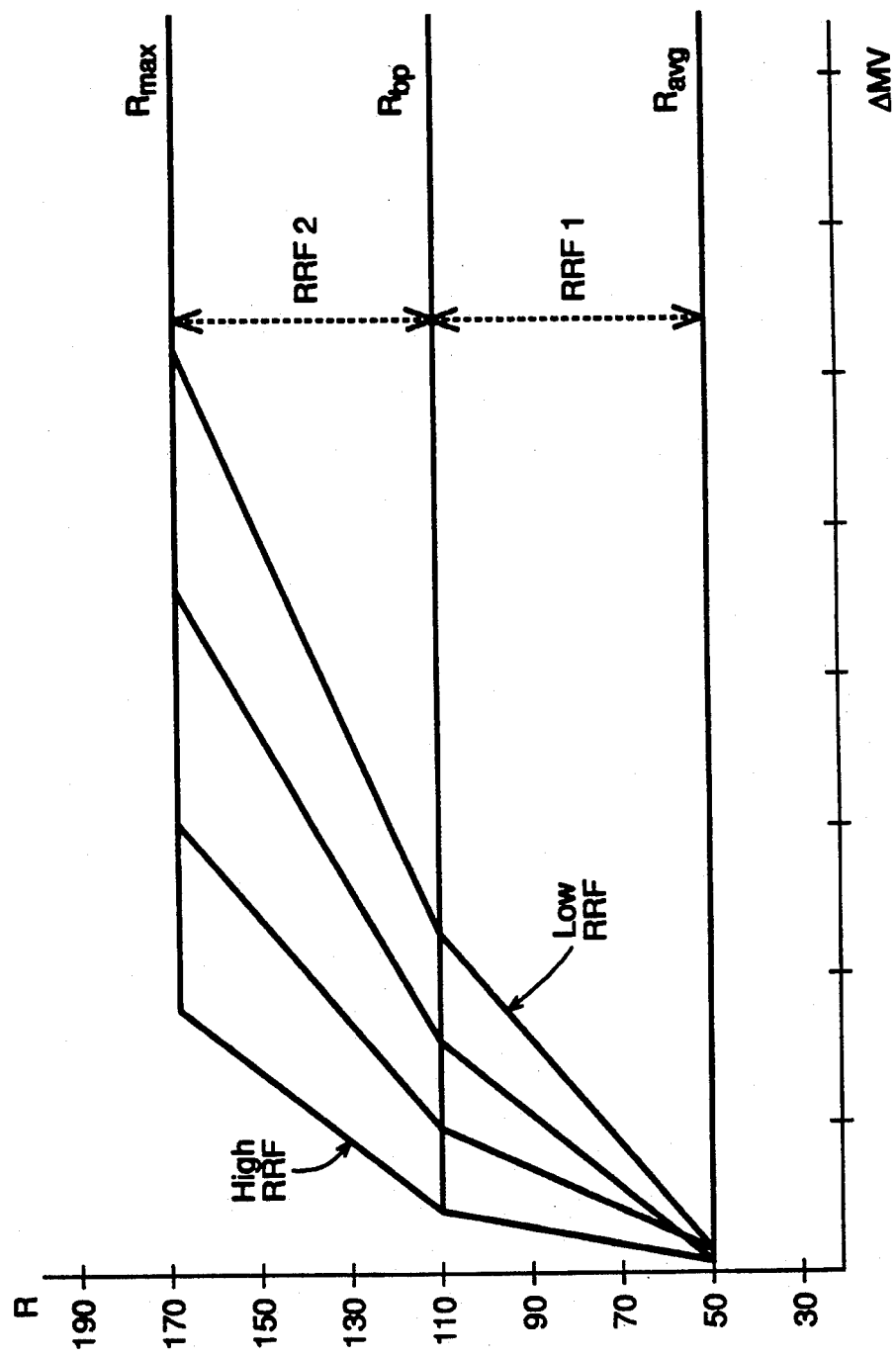
FIG. 8 is a graph which illustrates a plurality of dual slope rate response factors (RRF) for a minute volume metabolic indicator sensor which sets the relationship between minute volume and pacing rate and provides for an increase in the pacing rate at a patient's lower levels of exertion.

A metabolic rate response function of the present invention is enabled and disabled using telemetric programming. Prior to enabling a rate response function, a rate response factor (RRF) must be initialized. The RRF determines the degree of change in pacing rate that will occur for a particular change in the metabolic indicator measurement. FIG. 7 and FIG. 8 graphically illustrate two types of RRF relationships for a minute volume metabolic indicator parameter. FIG. 7 illustrates various RRF relationships of a linear slope RRF in which changes in pacing rate vary in a linear manner with respect to changes in minute volume. Four different RRF relationships are shown, a high RRF, a low RRF and two intermediate RRF correlations. FIG. 8 illustrates various RRF relationships of a dual linear slope RRF in which changes in pacing rate vary in a linear manner with respect to changes in minute volume within two ranges of pacing rate, with a different linear slope relating rate and minute volume in each range. In FIG. 8, like FIG. 7, four RRF relationships are shown.

The RRF may be initialized using one of two procedures. First, a physician may estimate the RRF for a patient and program that value into the pacemaker I of FIG. 1. In a second procedure, a physician may specify maximum and minimum pacing rates and enable the metabolic rate response function in an adapt mode, in which the minute volume is measured but the pacing rate does not change, and the patient may perform a peak exercise test by exercising to a maximum safe level. At the point of maximum minute volume, an external programmer reads the minute volume measurement via telemetric communication. The external programmer divides the maximum pacing rate by the minute volume measurement value to yield the RRF.

Figure 9:
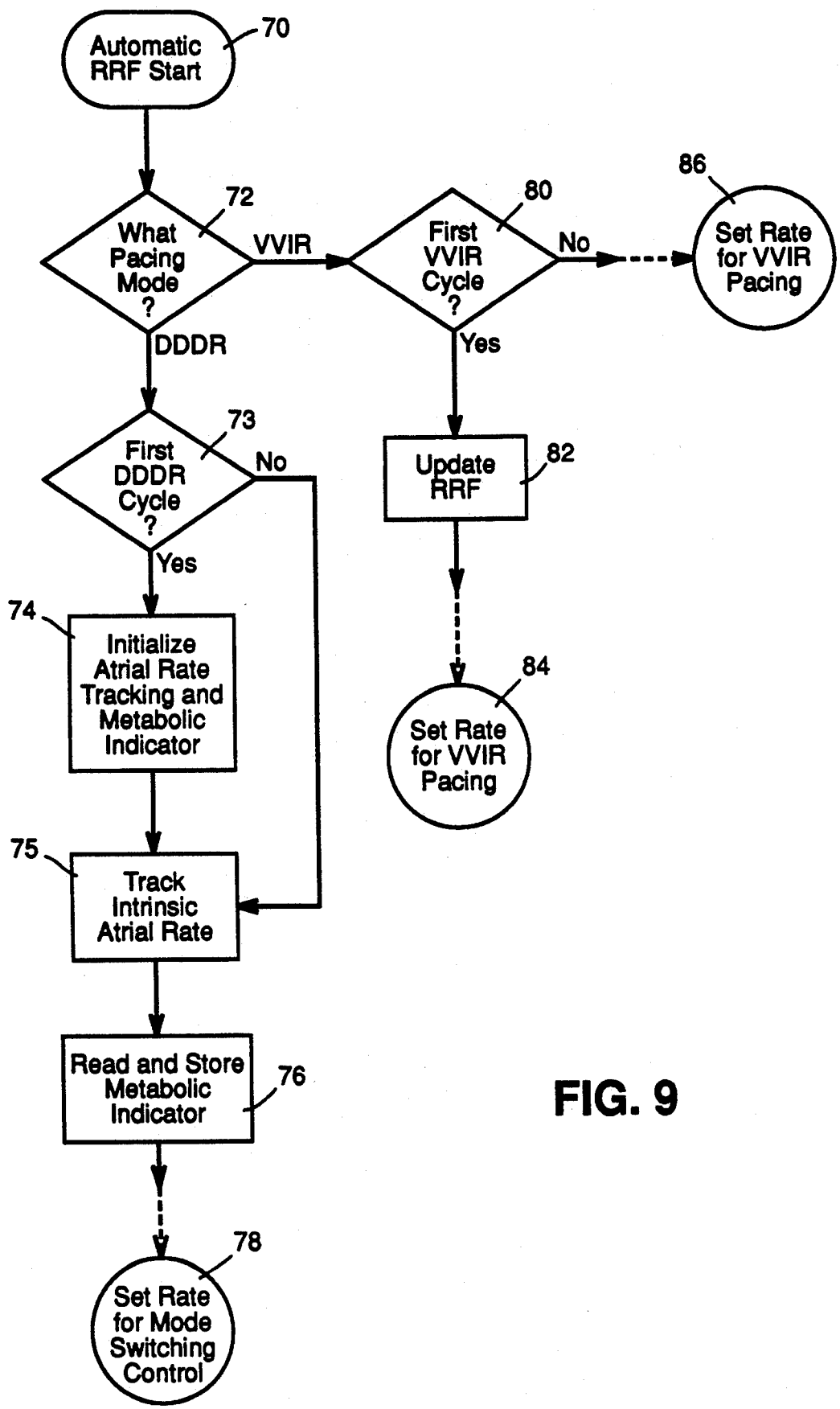
FIG. 9 is a flow diagram illustrating the operation of an automatic rate response factor function performed by the pacemaker of the present invention.
Figure 10:
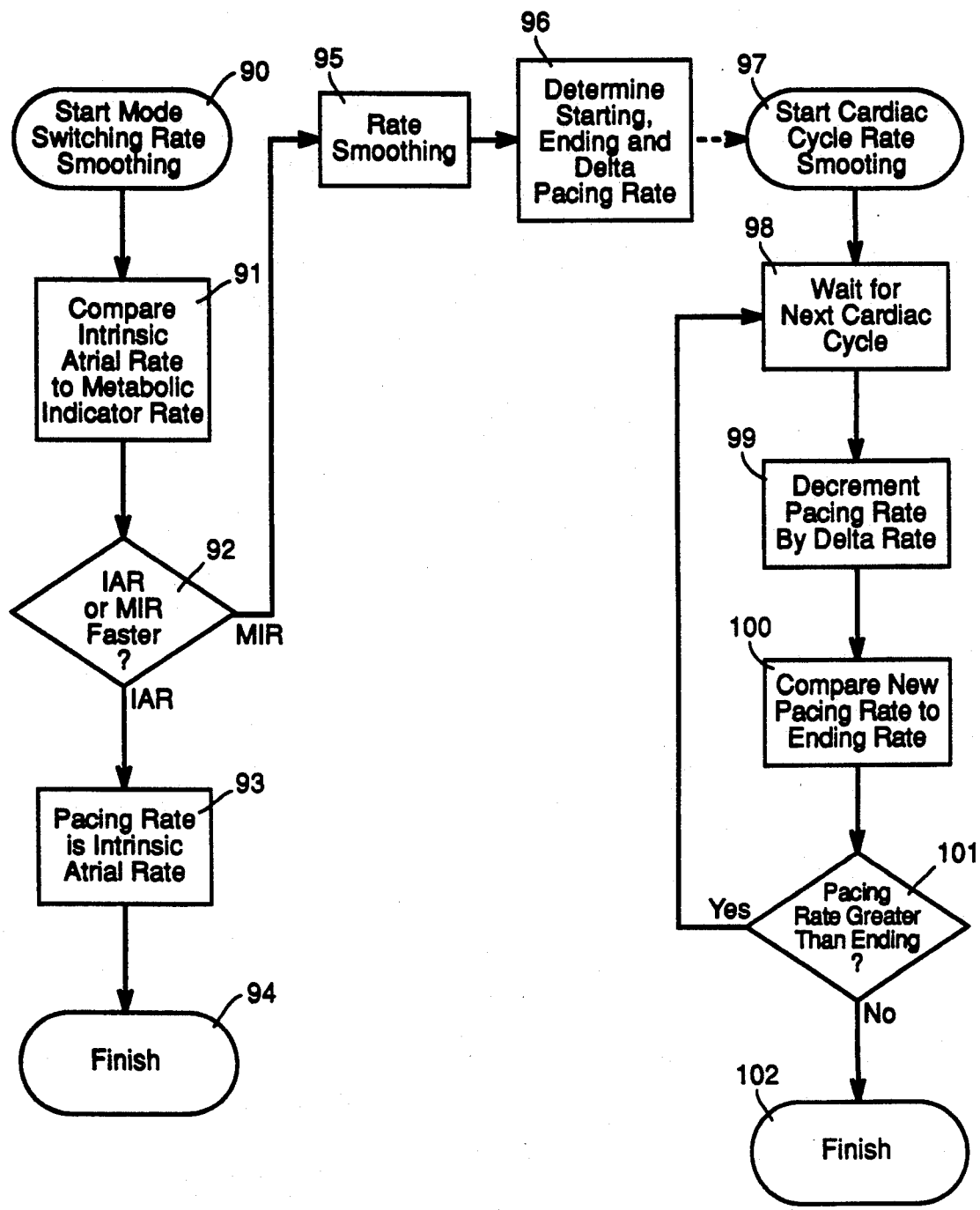
FIG. 10 is a flow diagram illustrating the operation of a rate smoothing function, which is associated with the mode switching operation performed by the pacemaker of the present invention.

FIG. 9 is a flow diagram which illustrates the steps of an automatic rate response factor (ARRF) operation, performed by the microprocessor 19 within the pacemaker 1 of FIG. 1. All operations are performed in an ARRF subroutine which operates during the update-cardiac-cycle-parameters block 115 of the cardiac cycle flow diagram of FIG. 6. The update-cardiac-cycle-parameters block 115 includes program instructions to call the ARRF subroutine and initiate the function in automatic-RRF-start block 70 of FIG. 9.

The ARRF operation to be performed depends on the current automatically set pacing mode, under the control of what-pacing-mode? logic block 72. At low intrinsic atrial rates, the pacemaker I normally functions in an A-V synchronous (DDDR) pacing mode in which the rate depends on the intrinsic atrial rate alone. In this mode, the pacing rate is not set to the metabolic indicator sensor rate, but rather the pacing rate is set by the intrinsic atrial rate. However, the metabolic indicator sensor continues to perform metabolic indicator measurements for two purposes. First, the atrial rate monitor discussed in conjunction with FIG. 6 uses these measurements to predict whether the intrinsic atrial rate is an appropriate heart rate for the patient's level of physical exertion. In addition, an automatic rate response factor operation uses the metabolic indicator measurements to automatically set the rate response factor (RRF). Therefore, while the pacemaker 1 is functioning in the DDDR mode, it determines instantaneous intrinsic atrial rates and metabolic indicator measurements for each cardiac cycle to find a reliable interrelation between the two parameters. The ARRF routine monitors the atrial rate in track-intrinsic-atrial-rate block 75. Block 75 may monitor atrial rate in various manners. For example, the microprocessor 19 within pacemaker 1 may determine and store the highest intrinsic atrial rate $R_{AVmax}$ (the shortest cardiac escape interval) at which, if occurring continuously, the pacemaker 1 would remain in A-V synchrony. The microprocessor 19 may store the $R_{AVmax}$ sample and, in read-and-store-metabolic-indicator block 76, the metabolic indicator measurement value which occurs during the $R_{AVmax}$ cardiac cycle. A convenient method for storing a parameter which relates the atrial rate for a single cardiac cycle is to store a code which specifies the escape interval of the cycle.

In the first DDDR cardiac cycle after performing a sequence of VVIR cycles, the pacemaker 1 initializes the intrinsic atrial rate and metabolic indicator measurement records under the control of a first-DDDR-cycle? logic block 73. In initialize-atrial-rate-tracking-and-metabolic-indicator block 74, the microprocessor 19 initializes the $R_{AVmax}$ and metabolic indicator measurement to zero when the pacing mode switches back to DDDR from VVIR operation when a high intrinsic atrial rate recovers to a moderate rate.

The foregoing illustrates an embodiment of the invention which, in track-intrinsic-atrial-rate block 75, employs the maximum intrinsic atrial rate $R_{AVmax}$ to set RRF. In another example, the microprocessor 19 may determine and store the intrinsic rate $R_{AVsync}$ (the shortest cardiac escape interval) occurring immediately previous to the occurrence of mode switching from DDDR to VVIR pacing. The microprocessor 19 may continuously store the $R_{AVsync}$ sample and the metabolic indicator measurement value which occurs during the $R_{AVsync}$ cardiac cycle while operating in the DDDR mode. Each sample replaces the most recent sample until mode switching occurs, at which time the last stored $R_{AVsync}$ and metabolic indicator measurement are used to set the pacing rate in a VVIR mode.

Furthermore, other methods for comparing intrinsic atrial rate and metabolic indicator measurements may be provided in track-intrinsic-atrial-rate block 75. For example, the pacemaker 1, while operating in a DDDR mode, may continuously determine and store intrinsic atrial rates and metabolic indicator measurements acquired during the same cardiac cycle. These paired data elements may be stored and, upon the occurrence of a fast intrinsic atrial rate which causes a mode switch to VVIR operation, the elements may be analyzed using curve fitting to determine an RRF slope.

In read-and-store-metabolic-indicator block 76, the microprocessor 19 may simply read the most recent metabolic indicator measurement result from RAM memory 56 of FIG. 3. For example, if the metabolic indicator sensor measures minute volume, then the metabolic parameter of interest is called delta minute volume $\Delta MV$, the difference between a short-term average and a long-term average minute volume (see U.S. Pat. No. 4,901,725). The microprocessor 19 can read the $\Delta MV$ memory location at any time and it will contain a relevant measurement for that cardiac cycle.

After performing read-and-store-metabolic-indicator block 76, the microprocessor 19 returns to the update-cardiac-cycle-parameters block 115 of FIG. 6 and uses the metabolic indicator measurement to predict whether the intrinsic atrial rate is an appropriate heart rate for the patient's level of physical exertion, as shown in set-rate-for-mode-switching-control block 78.

When the microprocessor 19 responds to a fast intrinsic atrial rate by switching from A-V synchronous mode to VVIR mode under the control of first-VVIR-cycle logic block 80, it automatically, in update-RRF block 82, sets the RRF equal to the difference between $R_{AVmax}$ and the programmed average pacing rate $R_{avg}$, with this difference divided by the metabolic indicator measurement, such as $\Delta MV$, taken during the cardiac cycle when $R_{AVmax}$ occurred. In the switching pacing cycle and subsequent pacing cycles, the microprocessor 19, in a corresponding one of set-rate-for-VVIR-pacing blocks 84 and 86, uses this RRF to determine the pacing rate in accordance with equation (1), below, as long as the intrinsic atrial rate remains high, so that the pacing mode remains VVIR:

$$R = RRF^* \Delta MV. \qquad (1)$$

When the intrinsic atrial rate recovers and the pacemaker 1 returns to DDDR operation, the same RRF is used to set the metabolic indicator rate and, in turn, the maximum atrial tracking rate, which the microprocessor 19 uses to analyze the intrinsic atrial rate to determine is mode switching is appropriate.

If the pacemaker 1 is programmed so that the RRF function is in the form of a dual linear slope (see FIG. 8), the microprocessor 19 first determines whether the highest intrinsic rate for A-V synchrony $R_{AVmax}$ is faster or slower than a predetermined and programmed breakpoint pacing rate $R_{bp}$. Thus, at the time that the pacemaker 1 switches operating mode from the A-V synchronous DDDR mode to the VVIR mode and if $R_{AVmax}$ is slower than $R_{bp}$, the microprocessor 19 sets a first slope $RRF_1$ equal to the difference between $R_{AVmax}$ and the programmed average pacing rate, with this difference divided by the cardiac cycle-associated metabolic indicator measurement, again using $\Delta MV$ as an example, in the manner of equation (2):

$$RRF_1 = (R_{AVmax} - R_{avg})/\Delta MV. \qquad (2)$$

Subsequently, while operating in the VVIR mode, the microprocessor 19 uses $RRF_1$ to set the VVIR pacing rate up to the breakpoint pacing rate $R_{bp}$. Thus, the pacing rate is set by multiplying $\Delta MV$ and $RRF_1$ for all $\Delta MV$ values up to a breakpoint delta minute volume value $\Delta MV_{bp}$, where $\Delta MV_{bp}$ is given by equation (3):

$$\Delta MV_{vp} = (R_p - R_{avg})^* \Delta MV)/(R_{AVmax} - R_{avg}). \qquad (3)$$

If a measured $\Delta MV$ value is greater than $\Delta MV_{bp}$, then the pacing rate is determined using the second slope $RRF_2$, which is determined at the time of switching from DDDR mode to VVIR mode pacing according to equation (4):

$$RRF_2 = (R_{max} - R_{bp})/(\Delta MV_{bp}) \qquad (4)$$

Where $R_{max}$ is a programmed maximum metabolic indicator rate and $\Delta MV_{max}$ is a programmed maximum delta minute volume metabolic indicator measurement.

Later while the pacemaker 1 is functioning in the VVIR mode, in set-rate-for-VVIR-pacing block 86, the pacing rate is determined using the second slope $RRF_2$ in accordance with equation (5)

$$R = ((\Delta MV - \Delta MV_{bp}) \cdot RRF_2) + R_{bp}. \quad (5)$$

If $R_{Avmax}$ is faster than $R_{bp}$ and the RRF is in the form of a dual linear slope, the microprocessor 19, for simplicity, may equate $R_{bp}$ to $R_{Avmax}$ and set a first slope $RRF_1$ equal to the difference between $R_{Avmax}$ and the programmed average pacing rate, with this difference divided by the cardiac-cycle-associated metabolic indicator measurement. Again using $\Delta MV$ as an example, at the time of switching from DDDR to VVIR mode, the microprocessor 19 performs the previously specified equation (2). Using the assumption of equality between $R_{Avmax}$ and $R_{bp}$, the $\Delta MV_{bp}$ equal to the $\Delta MV$ which was acquired during DDDR pacing and $RRF_2$ is similarly determined using equation (5).

Thus, after performing update-RRF block 82 in the first VVIR cycle or, in subsequent VVIR cardiac cycles, performing the first-VVIR-cycle? logic block 80, the microprocessor 19 returns to update-cardiac-cycle-parameters block 115 and, as indicated in set-rate-for-VVIR-pacing blocks 84 and 86, uses the metabolic indicator measurement to determine the pacing rate when the intrinsic atrial rate is too fast for A-V synchronous operation and the pacemaker 1 has switched to VVIR mode operation.

Once the patient returns to a normal intrinsic atrial rhythm, the intrinsic atrial rate may be different from the metabolic indicator rate at which the pacemaker 1 was pacing during the last cardiac cycle of VVIR pacing. A rate smoothing operation is illustrated in the flow diagram of FIG. 10 that sets an appropriate pacing rate when the two rate determining means differ. The rate smoothing operation is performed by the microprocessor 19 within the pacemaker 1 of FIG. 1. All rate smoothing operations are performed in a rate smoothing subroutine, beginning with start-mode-switching-rate-smoothing block 90, which occurs during the update-cardiac-cycle-parameters block 115 of the cardiac cycle flow diagram of FIG. 6. Compare-intrinsic-atrial-rate-to-metabolic-indicator-rate block 91 compares the two indications of appropriate pacing rate. If the intrinsic atrial rate is faster than the metabolic indicator rate, as determined by IAR-or-MIR-faster? logic block 92, then it should drive the pacing rate. This will occur inherently when the pacemaker 1 reverts to A-V synchronous pacing (VDD, DDD or DDDR), as shown in pacing-rate-is-intrinsic-atrial-rate block 93. However, if the metabolic indicator rate is faster than the intrinsic atrial rate, the microprocessor 19, in response to IAR-or-MIR-faster? logic block 92, will perform rate-smoothing block 95 to gradually reduce the pacing rate from the metabolic indicator rate to the intrinsic atrial rate.

The microprocessor 19 may be programmed to operate in an alternative mode in compare-intrinsic-atrial-rate-to-metabolic-indicator-rate block 91. Rather than comparing the intrinsic atrial rate to an automatically determined metabolic indicator rate, the microprocessor 19 may compare the intrinsic atrial rate to a programmed metabolic indicator rate value. Both the control code which determines the mode of operation in block 91 and the programmed metabolic indicator rate value are set via telemetric programming.

The microprocessor 19 initializes rate smoothing parameters in determine-starting-ending-and-delta-pacing-rate block 96. In one method of rate smoothing, the microprocessor 19 divides the difference between the metabolic indicator rate and the intrinsic atrial rate by a predetermined number of smoothing cardiac cycles. This number of smoothing cardiac cycles should be set to take into account how often occasional dropout heartbeats are expected to occur. For example, dropouts occur relatively often upon recovery from atrial fibrillation. The result is a smoothing rate delta, $\Delta R_8$. In the first subsequent DDDR pacing cycle, the starting pacing rate is set to the metabolic indicator rate. For each succeeding cardiac cycle, the pacing rate is set to the rate of the previous cycle less $\Delta R_8$, until the pacing rate is slower than the intrinsic atrial rate.

Alternatively, rate smoothing may be provided in a procedure which does not account for the likelihood of dropouts in particular pacing conditions, but is less complex to implement. For example, the starting pacing rate may begin at the metabolic indicator rate and be decreased by a predetermined and preprogrammed $\Delta R_8$ for each succeeding cardiac cycle until the pacing rate becomes slower than the ending pacing rate, the intrinsic atrial rate. The value of $\Delta R_8$ should be set to take into account the likelihood of occasional dropout heartbeats under most pacing conditions.

Using either method of rate smoothing, the implementation of smoothing on a cardiac cycle-by-cycle basis takes place starting with start-cardiac-cycle-rate-smoothing block 97. At a predetermined time within a cardiac cycle (preferably at the time of the update-cardiac-cycle-parameters block 115 of FIG. 6), set by operation of the wait-for-next-cardiac-cycle block 98, the microprocessor 19 updates the smoothed pacing rate in decrement-pacing-rate-by-delta-rate block 99 and compares the updated pacing rate to the ending pacing rate (the intrinsic atrial rate) in compare-new-pacing-rate-to-ending-rate block 100. Rate smoothing is finished when the pacing rate meets the ending rate, as shown in pacing-rate-greater-than-ending? logic block 101, when finish block 102 is reached.

Thus, it is shown from the foregoing that the present invention reliably, automatically and continuously determines a rate response factor that provides a true physiological correlation, rather than merely an estimated correlation, between a sensed metabolic indicator parameter and a metabolic demand pacing rate. The invention determines an appropriate rate response factor based on the true metabolic needs of the body, as indicated by the natural atrial rate, but only under circumstances in which the natural atrial rate is functioning in a reliable manner.

Although the invention has been described with reference to a particular embodiment, it is to be understood that this embodiment is merely illustrative of the application of the principles of the invention. Hence numerous modifications may be made therein and other arrangements may be devised without departing from the spirit and scope of the invention. For example, the described embodiment includes a control mechanism described as a microprocessor which may be replaced by any control circuitry capable of performing the same functions and operations.

What is claimed is:

1. A dual-chamber rate-responsive pacemaker, comprising:
   means for generating ventricular pacing pulses;

means for measuring metabolic indicator values;
means for determining metabolic indicator rates as a function of said metabolic indicator values and a predetermined rate response factor;
means for sensing atrial heartbeats;
means responsive to said atrial heartbeat sensing means for determining intrinsic atrial rate values;
means for ascertaining whether sensed atrial heartbeats are occurring at rates which are pathological, on one hand, and non-pathological, on the other hand;
means for storing at least one intrinsic atrial rate value and at least one metabolic indicator value when said ascertaining means has determined that the rate of atrial heartbeats is non-pathological; and
means for controlling said generating and sensing means to operate normally in a first mode in which ventricular pacing pulses are generated in synchrony with atrial heartbeats sensed by said sensing means but to switch to a second mode in which ventricular pacing pulses are generated at a rate which is a function of said metabolic indicator rates, with timing independent of said atrial heartbeats sensed by said sensing means, when said ascertaining means has determined that the rates of atrial heartbeats are pathological, said controlling means, upon switching from said first mode to said second mode, operating to update said rate response factor as a function of said stored at least one intrinsic atrial rate value and said stored at least one metabolic indicator value, and said controlling means, thereafter functioning in said second mode, operating to update said metabolic indicator rates as a function of said updated rate response factor and said stored metabolic indicator values.

2. A pacemaker in accordance with claim 1, wherein said means for measuring metabolic indicator values measures at least one metabolic indicator parameter selected from a group including respiratory minute volume, respiratory rate, QT interval, oxygen saturation, evoked potential, paced depolarization integral and core body temperature.

3. A pacemaker in accordance with claim 1, wherein said controlling means switches the operating mode from said second mode back to said first mode when said ascertaining means has determined that the rates of atrial heartbeats are again non-pathological, said pacemaker further comprising:
means, operational when said controlling means changes the operating mode from said second mode to said first mode, for comparing the intrinsic atrial rate values with the metabolic indicator rates; and
means, responsive to said comparing means and operative when the metabolic indicator rates are faster than the intrinsic atrial rate values, for controlling the rate of said pacing pulse generating means to gradually, over a plurality of cardiac cycles, reduce said rate from the metabolic indicator rates to the intrinsic atrial rates.

4. A pacemaker in accordance with claim 1, wherein said storing means stores a maximum intrinsic atrial rate value, and stores an associated metabolic indicator value measured during the cardiac cycle of the maximum intrinsic atrial rate value, when said ascertaining means has determined that the rate of atrial heartbeats is non-pathological, and wherein said controlling means updates said rate response factor as a function of said stored maximum intrinsic atrial rate value and said associated metabolic indicator value.

5. A pacemaker in accordance with claim 1, wherein said storing means stores an intrinsic atrial rate value during a cardiac cycle immediately preceding the cardiac cycle in which said controlling means changes the operating mode from said first mode to said second mode, and stores an associated metabolic indicator value measured during the cardiac cycle in which said intrinsic atrial rate value is stored, and wherein said controlling means updates said rate response factor as a function of said stored intrinsic atrial rate value and said associated metabolic indicator value.

6. A pacemaker in accordance with claim 1, wherein said storing means stores a plurality of intrinsic atrial rate values and a plurality of associated metabolic indicator values, measured during the cardiac cycles of the plurality of intrinsic atrial rate values when said ascertaining means has determined that the rate of atrial heartbeats is non-pathological, and wherein said controlling means updates said rate response factor as a function of said plurality of stored intrinsic atrial rate values and said plurality of associated metabolic indicator values.

7. A pacemaker in accordance with claim 1, wherein said controlling means switches the operating mode from said second mode back to said first mode when said ascertaining means has determined that the rates of atrial heartbeats are again non-pathological and the intrinsic atrial rate values are faster than the metabolic indicator rates, and wherein said controlling means switches operating modes from said second mode to a third mode when said ascertaining means has determined that the rates of atrial heartbeats are again non-pathological and the metabolic indicator rates are faster than the intrinsic atrial rate values, said third mode being one in which ventricular pacing pulses are generated at a rate which is gradually reduced, on a cardiac cycle by cycle basis, from the metabolic indicator rates to the intrinsic atrial rate values.

8. A pacemaker in accordance with claim 1, wherein said ascertaining means distinguishes pathological atrial rates from non-pathological atrial rates on the basis of the value of the current metabolic indicator rate.

9. A pacemaker in accordance with claim 1, wherein said ascertaining means distinguishes pathological atrial rates from non-pathological atrial rates on the basis of a programmed atrial rate limit.

10. A dual-chamber rate-responsive pacemaker, comprising:
means for generating atrial and ventricular pacing pulses;
means for sensing atrial and ventricular heartbeats;
means responsive to said sensing means for determining intrinsic atrial rate values;
means for measuring metabolic indicator values;
means for determining metabolic indicator rates as a function of said metabolic indicator values and a predetermined rate response factor;
means for ascertaining whether sensed atrial heartbeats are occurring at a rate which is pathological, on one hand, and non-pathological, on the other hand;
means for storing at least one intrinsic atrial rate value and at least one metabolic indicator parameter when said ascertaining means has determined that the rate of atrial heartbeats is non-pathological; and means for controlling said generating and sensing means to operate normally in a DDDR mode but to switch to a VVIR mode when the rate of atrial heartbeats is pathological, said controlling means, upon switching from the DDDR mode to the VVIR mode, operating to update said rate response factor as a function of said stored at least one intrinsic atrial rate value and said stored at least one metabolic indicator parameter, and said controlling means, thereafter functioning in the VVIR mode, operating to update said metabolic indicator rates as a function of said updated rate response factor and said stored metabolic indicator parameter.

11. A pacemaker in accordance with claim 10, wherein said means for measuring metabolic indicator values measures at least one metabolic indicator parameter selected from a group including respiratory minute volume, respiratory rate, QT interval, oxygen saturation, evoked potential, paced depolarization integral and core body temperature.

12. A pacemaker in accordance with claim 10, wherein said ascertaining means distinguishes pathological atrial rates from non-pathological atrial rates on the basis of the value of the current metabolic indicator rate.

13. A pacemaker in accordance with claim 10, wherein said ascertaining means distinguishes pathological atrial rates from non-pathological atrial rates on the basis of a programmed atrial rate limit.

14. A pacemaker in accordance with claim 10, wherein said controlling means switches the operating mode from said VVIR mode back to said DDDR mode when said ascertaining means has determined that the rates of atrial heartbeats are again non-pathological, said pacemaker further comprising:
   means, operational when said controlling means changes operating mode from said VVIR mode to said DDDR mode, for comparing the intrinsic atrial rate values with the metabolic indicator rates; and
   means, responsive to said comparing means and operative when the metabolic indicator rates are faster than the intrinsic atrial rate values, for controlling the rate of said pacing pulse generating means to gradually, over a plurality of cardiac cycles, reduce said rate from the metabolic indicator rates to the intrinsic atrial rates.

15. A pacemaker in accordance with claim 10, wherein said storing means stores a maximum intrinsic atrial rate value, and stores an associated metabolic indicator value measured during the cardiac cycle of the maximum intrinsic atrial rate value, when said ascertaining means has determined that the rate of atrial heartbeats is non-pathological, and wherein said controlling means updates said rate response factor as a function of said stored maximum intrinsic atrial rate value and said associated metabolic indicator value.

16. A pacemaker in accordance with claim 10, wherein said storing means stores an intrinsic atrial rate value during a cardiac cycle immediately preceding the cardiac cycle in which said controlling means changes the operating mode from said DDDR mode to said VVIR mode, and stores an associated metabolic indicator value measured during the cardiac cycle in which said intrinsic atrial rate value is stored, and wherein controlling means updates said rate response factor as a function of said stored intrinsic atrial rate value and said associated metabolic indicator value.

17. A pacemaker in accordance with claim 10, wherein said storing means stores a plurality of intrinsic atrial rate values and a plurality of associated metabolic indicator values, measured during the cardiac cycles of the plurality of intrinsic atrial rate values when said ascertaining means has determined that the rate of atrial heartbeats is non-pathological, and wherein said controlling means updates said rate response factor as a function of said plurality of stored intrinsic atrial rate values and said plurality of associated metabolic indicator values.

18. A pacemaker in accordance with claim 10, wherein said controlling means switches the operating mode from said VVIR mode back to said DDDR mode when said ascertaining means has determined that the rates of atrial heartbeats are again non-pathological and the intrinsic atrial rate values are faster than the metabolic indicator rates, and wherein said controlling means switches the operating mode from said VVIR mode to a DDDR mode, in which atrial pacing pulses are generated at a rate which is gradually reduced, on a cardiac cycle by cycle basis, from the metabolic indicator rates to the intrinsic atrial rate values, when said ascertaining means has determined that the rates of atrial heartbeats are again non-pathological and the metabolic indicator rates are faster than the intrinsic atrial rate values.

19. A dual-chamber rate-responsive pacemaker, comprising:
   means for generating ventricular pacing pulses;
   means for sensing atrial heartbeats;
   means responsive to said atrial heartbeat sensing means for determining an intrinsic atrial rate;
   means for measuring metabolic indicator values;
   means for determining a metabolic indicator rate as a function of said metabolic indicator values and a predetermined, continuously updating, rate response factor;
   means for comparing said metabolic indicator rate to said intrinsic atrial rate to determine whether said intrinsic atrial rate is pathological;
   means for controlling said generating and sensing means to operate in a first, synchronous, mode in which said ventricular pacing pulse generating means generates paces in synchrony with the atrial heartbeats sensed by said sensing means when said intrinsic atrial rate is non-pathological, and otherwise controlling said generating and sensing means to operate in a second, nonsynchronous, mode in which said ventricular pacing pulse generating means generates paces at said metabolic indicator rate;
   means, operational when said controlling means changes the operating mode from said first mode to said second mode, for correlating the metabolic indicator values measured by said measuring means and the intrinsic atrial rate determined by said intrinsic atrial rate determining means while the pacemaker is operating in said first mode; and
   means responsive to said correlating means for updating said rate response factor.

20. A pacemaker in accordance with claim 19, wherein said means for measuring metabolic indicator values measures at least one metabolic indicator parameter selected from a group including respiratory minute volume, respiratory rate, QT interval, oxygen saturation, evoked potential, paced depolarization integral and core body temperature.

21. A pacemaker in accordance with claim 19, wherein said controlling means switches the operating mode from said second mode back to said first mode when said ascertaining means has determined that the rates of atrial heartbeats are again non-pathological, said pacemaker further comprising:
   means, operational when said controlling means changes the operating mode from said second mode to said first mode, for comparing the intrinsic atrial rate values with the metabolic indicator rates; and
   means, responsive to said comparing means and operative when the metabolic indicator rates are faster than the intrinsic atrial rate values, for controlling the rate of said pacing pulse generating means to gradually, over a plurality of cardiac cycles, reduce said rate from the metabolic indicator rates to the intrinsic atrial rates.

22. A pacemaker in accordance with claim 19, wherein said correlating means evaluates a maximum intrinsic atrial rate value and an associated metabolic indicator value measured during the cardiac cycle of said maximum intrinsic atrial rate value, and said updating means updates said rate response factor as a function of said maximum intrinsic atrial rate value and said associated metabolic indicator value.

23. A pacemaker in accordance with claim 19, wherein said correlating means evaluates an intrinsic atrial rate value during a cardiac cycle immediately preceding the cardiac cycle in which said controlling means changes the operating mode from said first mode to said second mode, and stores an associated metabolic indicator value measured during the cardiac cycle in which said intrinsic atrial rate value is stored, and wherein said updating means updates said rate response factor as a function of said stored intrinsic aerial rate value and said associated metabolic indicator value.

24. A pacemaker in accordance with claim 19, wherein said correlating means evaluates a plurality of intrinsic atrial rate values and a plurality of associated metabolic indicator values, measured during the cardiac cycles of the plurality of intrinsic atrial rate values, and wherein said updating means updates said rate response factor as a function of said plurality of stored intrinsic atrial rate values and said plurality of associated metabolic indicator values.

25. A pacemaker in accordance with claim 19, wherein said controlling means switches the operating mode from said second mode back to said first mode when said ascertaining means has determined that the rates of atrial heartbeats are again non-pathological and the intrinsic atrial rate is faster than the metabolic indicator rate, and wherein said controlling means switches the operating mode from said second mode to a third mode when said ascertaining means has determined that the rates of atrial heartbeats are again non-pathological and the metabolic indicator rate is faster than the intrinsic atrial rate, said third mode being one in which ventricular pacing pulses are generated at a rate which is gradually reduced, on a cardiac cycle by cardiac cycle basis, from the metabolic indicator rate to the intrinsic atrial rate.

26. A method of operating a dual-chamber rate-responsive pacemaker, comprising the steps of:
   generating ventricular pacing pulses;
   sensing atrial heartbeats;
   determining an intrinsic atrial rate in response to said atrial heartbeat sensing step;
   measuring metabolic indicator values;
   determining a metabolic indicator rate as a function of the metabolic indicator values and a predetermined, continuously updating, rate response factor;
   comparing said metabolic indicator rate to said intrinsic atrial rate to determine whether said intrinsic atrial rate is pathological;
   controlling said generating and sensing steps to operate in a first, synchronous, mode in which said generating step generates ventricular pacing pulses in synchrony with the atrial heartbeats sensed by said sensing step when the intrinsic atrial rate is non-pathological, and otherwise controlling said generating and sensing steps to operate in a second, nonsynchronous, mode in which said generating step generates ventricular pacing pulses at the metabolic indicator rate;
   when said controlling step changes the operating mode from said first mode to said second mode, correlating the metabolic indicator values measured by said measuring step and the intrinsic atrial rate determined by said intrinsic atrial rate determining step while the pacemaker was operating in said first mode; and
   updating said rate response factor in response to the result of said correlating step.

27. A method in accordance with claim 26, wherein said step of measuring metabolic indicator values includes the substep of measuring at least one metabolic indicator parameter selected from a group including respiratory minute volume, respiratory rate, QT interval, oxygen saturation, evoked potential, paced depolarization integral and core body temperature.

28. A method in accordance with claim 26, further comprising:
   comparing the intrinsic atrial rate values with the metabolic indicator rates when said controlling step changes the operating mode back from said second mode to said first mode; and
   controlling the rate of said pacing pulse generating step to gradually, over a plurality of cardiac cycles, reduce said rate from the metabolic indicator rates to the intrinsic atrial rates in response to said comparing step and operative when the metabolic indicator rates are faster than the intrinsic atrial rate values.

29. A method in accordance with claim 26, wherein said correlating step includes the substep of evaluating a maximum intrinsic atrial rate value and an associated metabolic indicator value measured during the cardiac cycle of said maximum intrinsic atrial rate value, and wherein said updating step includes the substep of updating said rate response factor as a function of said maximum intrinsic atrial rate value and said associated metabolic indicator value.

30. A method in accordance with claim 26, wherein said correlating step includes the substeps of evaluating an intrinsic atrial rate value during a cardiac cycle immediately preceding the cardiac cycle in which said controlling step changes the operating mode from said first mode to said second mode, and storing an associated metabolic indicator value measured during the cardiac cycle in which said intrinsic atrial rate value is stored, and wherein said updating step includes the substep of updating said rate response factor as a function of said stored intrinsic atrial rate value and said associated metabolic indicator value.

31. A method in accordance with claim 26, wherein said correlating step includes the substep of evaluating a plurality of intrinsic atrial rate values and a plurality of associated metabolic indicator values, measured during the cardiac cycles of the plurality of intrinsic atrial rate values, and wherein said updating step includes the substep of updating said rate response factor as a function of said plurality of stored intrinsic atrial rate values and said plurality of associated metabolic indicator values.

32. A method in accordance with claim 26, wherein said controlling step includes the substep of switching operating modes from said second mode back to said first mode when said comparing step has determined that the rates of atrial heartbeats are again non-pathological and the intrinsic atrial rate values are faster than the metabolic indicator rates, and wherein said controlling step includes the substep, of switching operating modes from said second mode to a third mode when said comparing step has determined that the rates of atrial heartbeats are again non-pathological and the metabolic indicator rates are faster than the intrinsic atrial rate values, said third mode being one in which ventricular pacing pulses are generated at a rate which is gradually reduced, on a cardiac cycle by cycle basis, from the metabolic indicator rates to the intrinsic atrial rate values.

33. A method of operating a dual-chamber rate-responsive pacemaker, comprising the steps of:
generating atrial and ventricular pacing pulses;
sensing atrial and ventricular heartbeats;
determining intrinsic atrial rate values in response to said sensing step;
measuring metabolic indicator values;
determining metabolic indicator rates as a function of said metabolic indicator values and a predetermined rate response factor;
ascertaining whether sensed atrial heartbeats are occurring at a rate which is pathological, on one hand, and non-pathological, on the other hand;
storing at least one intrinsic atrial rate value and at least one metabolic indicator parameter when said ascertaining step has determined that the rate of atrial heartbeats is non-pathological; and
controlling said generating and sensing steps to operate normally in a DDDR mode but to switch to a VVIR mode when the rate of atrial heartbeats is pathological, said controlling step, upon switching from the DDDR mode to the VVIR mode, operating to update said rate response factor as a function of said stored at least one intrinsic atrial rate value and said stored at least one metabolic indicator parameter, and said controlling step, thereafter functioning in the VVIR mode, operating to update said metabolic indicator rates as a function of said updated rate response factor and said stored metabolic indicator parameter.

34. A method in accordance with claim 33, wherein said step of measuring metabolic indicator values includes the substep of measuring at least one metabolic indicator parameter selected from a group including respiratory minute volume, respiratory rate, QT interval, oxygen saturation, evoked potential, paced depolarization integral and core body temperature.

35. A method in accordance with claim 33, wherein said ascertaining step includes the substep of distinguishing pathological atrial rates from non-pathological atrial rates on the basis of the value of the current metabolic indicator rate.

36. A method in accordance with claim 33, wherein said ascertaining step includes the substep of distinguishing pathological atrial rates from non-pathological atrial rates on the basis of a programmed atrial rate limit.

37. A method in accordance with claim 33, wherein said controlling step includes the substep of switching the operating mode from said VVIR mode back to said DDDR mode when said ascertaining step determines that the rate of atrial heartbeats is again non-pathological, and further comprising:
comparing the intrinsic atrial rate values with the metabolic indicator rates when said controlling step changes operating mode from said VVIR mode to said DDDR mode; and
controlling the rate of said pacing pulse generating step to gradually, over a plurality of cardiac cycles, reduce the rate from the metabolic indicator rates to the intrinsic atrial rates in response to said comparing step and operative when the metabolic indicator rates are faster than the intrinsic atrial rate values.

38. A method in accordance with claim 33, wherein said storing step includes the substeps of storing a maximum intrinsic atrial rate value, and storing an associated metabolic indicator value measured during the cardiac cycle of the maximum intrinsic atrial rate value, when said ascertaining step has determined that the rate of atrial heartbeats is non-pathological, and wherein said controlling step includes the substep of updating said rate response factor as a function of said stored maximum intrinsic atrial rate value and said associated metabolic indicator value.

39. A method in accordance with claim 33, wherein said storing step includes the substeps of storing an intrinsic atrial rate value during a cardiac cycle immediately preceding the cardiac cycle in which said controlling step changes the operating mode from said DDDR mode to said VVIR mode, and storing an associated metabolic indicator value measured during the cardiac cycle in which said intrinsic atrial rate value is stored, and wherein said controlling step includes the substeps of updating said rate response factor as a function of said stored intrinsic atrial rate value and said associated metabolic indicator value.

40. A method in accordance with claim 33, wherein said storing step includes the substep of storing a plurality of intrinsic atrial rate values and a plurality of associated metabolic indicator values, measured during the cardiac cycles of the plurality of intrinsic atrial rate values when said ascertaining step has determined that the rate of atrial heartbeats is non-pathological, and wherein said controlling step includes the substep of updating said rate response factor as a function of said plurality of stored intrinsic atrial rate values and said plurality of associated metabolic indicator values.

41. A method in accordance with claim 33, wherein said controlling step includes the substeps of switching the operating mode from said VVIR mode back to said DDDR mode when said ascertaining step has determined that the rates of atrial heartbeats are again non-pathological and the intrinsic atrial rate values are faster than the metabolic indicator rates, and switching the operating mode from said VVIR mode to a DDDR mode in which atrial pacing pulses are generated at a rate which is gradually reduced, on a cardiac cycle by cycle basis, from said metabolic indicator rates to said intrinsic atrial rate values when said ascertaining step has determined that the rates of atrial heartbeats are again non-pathological and the metabolic indicator rates are faster than said intrinsic atrial rate values.

42. A method of operating a dual-chamber rate-responsive pacemaker, comprising the steps of:
generating ventricular pacing pulses;
measuring metabolic indicator values;
determining metabolic indicator rates as a function of said metabolic indicator values and a predetermined rate response factor;
sensing atrial heartbeats;
determining intrinsic atrial rate values in response to said atrial heartbeat sensing step;
ascertaining whether sensed atrial heartbeats are occurring at rates which are pathological, on one hand, and non-pathological;
storing at least one intrinsic atrial rate value and at least one metabolic indicator value when said ascertaining step has determined that the rate of atrial heartbeats is non-pathological; and
controlling said generating and sensing steps to operate normally in a first mode in which ventricular pacing pulses are generated in synchrony with atrial heartbeats sensed in said sensing step but to switch to a second mode in which ventricular pacing pulses are generated at a rate which is a function of said metabolic indicator rates, with timing independent of said atrial heartbeats sensed by said sensing step, when said ascertaining step has determined that the rates of atrial heartbeats are pathological, said controlling step, upon switching from said first mode to said second mode, operating to update said rate response factor as a function of said stored at least one intrinsic atrial rate value and said stored at least one metabolic indicator value, and said controlling step, thereafter functioning in said second mode, operating to update said metabolic indicator rates as a function of said updated rate response factor and said stored metabolic indicator values.

43. A method in accordance with claim 42, wherein said step of measuring metabolic indicator values includes the substep of measuring at least one metabolic indicator parameter selected from a group including respiratory minute volume, respiratory rate, QT interval, oxygen saturation, evoked potential, paced depolarization integral and core body temperature.

44. A method in accordance with claim 42, wherein said ascertaining step includes the substep of distinguishing pathological atrial rates from non-pathological atrial rates on the basis of the value of the current metabolic indicator rate.

45. A method in accordance with claim 42, wherein said ascertaining step includes the substep of distinguishing pathological atrial rates from non-pathological atrial rates on the basis of a programmed atrial rate limit.

46. A method in accordance with claim 42, wherein said controlling step includes the substep of switching the operating mode from said second mode back to said first mode when said ascertaining step determines that the rate of atrial heartbeats is again non-pathological, and further comprising:
comparing the intrinsic atrial rate values with the metabolic indicator rates when said controlling step changes the operating mode from said second mode to said first mode; and
controlling the rate of said pacing pulse generating step to gradually, over a plurality of cardiac cycles, reduce the rate from the metabolic indicator rates to the intrinsic atrial rates in response to said comparing step and operative when the metabolic indicator rates are faster than the intrinsic atrial rate values.

47. A method in accordance with claim 42, wherein said storing step includes the substep of storing a maximum intrinsic atrial rate value and an associated metabolic indicator value measured during the cardiac cycle of the maximum intrinsic atrial rate value when said ascertaining step has determined that the rate of atrial heartbeats is non-pathological, and wherein said controlling step includes the substep of updating said rate response factor as a function of said stored maximum intrinsic atrial rate value and said associated metabolic indicator value.

48. A method in accordance with claim 42, wherein said storing step includes the substeps of storing an intrinsic atrial rate value during a cardiac cycle immediately preceding the cardiac cycle in which said controlling step changes the operating mode from said first mode to said second mode, and storing an associated metabolic indicator value measured during the cardiac cycle in which said intrinsic atrial rate value is stored, and wherein said controlling step includes the substep of updating said rate response factor as a function of said stored intrinsic atrial rate value and said associated metabolic indicator value.

49. A method in accordance with claim 42, wherein said storing step includes the substep of storing a plurality of intrinsic atrial rate values and a plurality of associated metabolic indicator values, measured during the cardiac cycles of the plurality of intrinsic atrial rate values when said ascertaining step has determined that the rate of atrial heartbeats is non-pathological, and wherein said controlling step includes the substep of updating said rate response factor as a function of said plurality of stored intrinsic atrial rate values and said plurality of associated metabolic indicator values.

50. A method in accordance with claim 42, wherein said controlling step includes the substeps of switching the operating mode from said second mode back to said first mode when said ascertaining step has determined that the rates of atrial heartbeats are again non-pathological and the intrinsic atrial rate is faster than the metabolic indicator rate, and switching the operating mode from said second mode to a third mode when said ascertaining step has determined that the rates of atrial heartbeats are again non-pathological and the metabolic indicator rate is faster than the intrinsic atrial rate, said third mode being one in which ventricular pacing pulses are generated at a rate which is gradually reduced, on a cardiac cycle by cycle basis, from the metabolic indicator rate to the intrinsic atrial rate.

* * * * *